(12) United States Patent
Barron et al.

(10) Patent No.: US 11,878,084 B2
(45) Date of Patent: Jan. 23, 2024

(54) DISINFECTING LIGHT EMITTING SUBCOMPONENT

(71) Applicant: Vyv, Inc., Latham, NY (US)

(72) Inventors: Robert Barron, Boulder, CO (US); Cori Winslow, Rensselaer, NY (US); Jorel Lalicki, Troy, NY (US); James Peterson, Falls Church, VA (US)

(73) Assignee: Vyv, Inc., Latham, NY (US)

(*) Notice: Subject to any disclaimer, the term of this patent is extended or adjusted under 35 U.S.C. 154(b) by 2 days.

(21) Appl. No.: 16/577,766

(22) Filed: Sep. 20, 2019

(65) Prior Publication Data

US 2021/0085810 A1 Mar. 25, 2021

(51) Int. Cl.
*A61L 2/08* (2006.01)
*A61L 2/24* (2006.01)

(52) U.S. Cl.
CPC .......... *A61L 2/084* (2013.01); *A61L 2/24* (2013.01); *A61L 2202/11* (2013.01); *A61L 2202/14* (2013.01)

(58) Field of Classification Search
CPC ...................................................... A61L 2/084
USPC ............................................................. 422/30
See application file for complete search history.

(56) References Cited

U.S. PATENT DOCUMENTS

| | | | |
|---|---|---|---|
| 1,493,820 A | 5/1924 | Miller et al. | |
| 2,622,409 A | 12/1952 | Stimkorb | |
| 2,773,715 A | 12/1956 | Lindner | |
| 3,314,746 A | 4/1967 | Millar | |
| 3,670,193 A | 6/1972 | Thorington et al. | |
| 3,791,864 A | 2/1974 | Steingroever | |
| 3,926,556 A | 12/1975 | Boucher | |
| 3,992,646 A | 11/1976 | Corth | |
| 4,121,107 A | 10/1978 | Bachmann | |
| 4,461,977 A | 7/1984 | Pierpoint et al. | |

(Continued)

FOREIGN PATENT DOCUMENTS

| | | |
|---|---|---|
| CN | 1932370 A | 3/2007 |
| CN | 201396611 Y | 2/2010 |

(Continued)

OTHER PUBLICATIONS

Brennesholtz et al., Projection Displays 2nd Edition, 2008, Wiley, pp. 365-368 (Year: 2009).*

(Continued)

*Primary Examiner* — Holly Kipouros
(74) *Attorney, Agent, or Firm* — Banner & Witcoff, Ltd.

(57) ABSTRACT

Methods, systems, and apparatuses involving disinfecting light subcomponents are provided. An example system comprises a substrate with one or more light emitters disposed on the substrate. The one or more light emitters may be configured to inactivate microorganisms on a surface by emitting light. The light may comprise a proportion of spectral energy of the light, measured in a 380 nanometers (nm) to 420 nm wavelength range, greater than 50%. The light may comprise a full width half max (FWHM) emission spectrum of less than 20 nm and centered at a wavelength of approximately 405 nm to concentrate a spectral energy of the light and minimize energy associated with wavelengths that bleed into an ultraviolet wavelength range. The light may comprise an irradiance at the surface sufficient to initiate inactivation of microorganisms on the surface.

24 Claims, 8 Drawing Sheets

(56) References Cited

U.S. PATENT DOCUMENTS

| | | |
|---|---|---|
| 4,576,436 A | 3/1986 | Daniel |
| 4,867,052 A | 9/1989 | Cipelletti |
| 4,892,712 A | 1/1990 | Robertson et al. |
| 4,910,942 A | 3/1990 | Dunn et al. |
| 5,231,472 A | 7/1993 | Marcus et al. |
| 5,489,827 A | 2/1996 | Xia |
| 5,530,322 A | 6/1996 | Ference et al. |
| 5,559,681 A | 9/1996 | Duarte |
| 5,668,446 A | 9/1997 | Baker |
| 5,721,471 A | 2/1998 | Begemann et al. |
| 5,725,148 A | 3/1998 | Hartman |
| 5,800,479 A | 9/1998 | Thiberg |
| 5,901,564 A | 5/1999 | Comeau, II |
| 5,915,279 A | 6/1999 | Cantrall et al. |
| 5,962,989 A | 10/1999 | Baker |
| 5,968,766 A | 10/1999 | Powers |
| 6,031,958 A | 2/2000 | McGaffigan |
| 6,166,496 A | 12/2000 | Lys et al. |
| 6,183,500 B1 | 2/2001 | Kohler |
| 6,242,752 B1 | 6/2001 | Soma et al. |
| 6,246,169 B1 | 6/2001 | Pruvot |
| 6,251,127 B1 | 6/2001 | Biel |
| 6,379,022 B1 | 4/2002 | Amerson et al. |
| 6,477,853 B1 | 11/2002 | Khorram |
| 6,524,529 B1 | 2/2003 | Horton, III |
| 6,551,346 B2 | 4/2003 | Crossley |
| 6,554,439 B1 | 4/2003 | Teicher et al. |
| 6,627,730 B1 | 9/2003 | Burnie |
| 6,676,655 B2 | 1/2004 | McDaniel |
| 6,791,259 B1 | 9/2004 | Stokes et al. |
| 6,902,807 B1 | 6/2005 | Argoitia et al. |
| 7,015,636 B2 | 3/2006 | Bolta |
| 7,175,807 B1 | 2/2007 | Jones |
| 7,190,126 B1 | 3/2007 | Paton |
| 7,198,634 B2 | 4/2007 | Harth et al. |
| 7,201,767 B2 | 4/2007 | Bhullar |
| 7,213,941 B2 | 5/2007 | Sloan et al. |
| 7,438,719 B2 | 10/2008 | Chung et al. |
| 7,476,885 B2 | 1/2009 | Garcia et al. |
| 7,503,675 B2 | 3/2009 | Demarest et al. |
| 7,516,572 B2 | 4/2009 | Yang et al. |
| 7,521,875 B2 | 4/2009 | Maxik |
| 7,611,156 B2 | 11/2009 | Dunser |
| 7,612,492 B2 | 11/2009 | Lestician |
| 7,658,891 B1 | 2/2010 | Barnes |
| 7,955,695 B2 | 6/2011 | Argoitia |
| 8,035,320 B2 | 10/2011 | Sibert |
| 8,214,084 B2 | 7/2012 | Ivey et al. |
| 8,232,745 B2 | 7/2012 | Chemel et al. |
| 8,357,914 B1 | 1/2013 | Caldwell |
| 8,398,264 B2 | 3/2013 | Anderson et al. |
| 8,467,052 B1 | 6/2013 | Chao et al. |
| 8,476,844 B2 | 7/2013 | Hancock et al. |
| 8,481,970 B2 | 7/2013 | Cooper et al. |
| 8,506,612 B2 | 8/2013 | Ashdown |
| 8,508,204 B2 | 8/2013 | Deurenberg et al. |
| 8,761,565 B1 | 6/2014 | Coleman et al. |
| 8,886,361 B1 | 11/2014 | Harmon et al. |
| 8,895,940 B2 | 11/2014 | Moskowitz et al. |
| 8,999,237 B2 | 4/2015 | Tumanov |
| 9,024,276 B2 | 5/2015 | Pugh et al. |
| 9,027,479 B2 | 5/2015 | Raksha et al. |
| 9,028,084 B2 | 5/2015 | Maeng et al. |
| 9,039,966 B2 | 5/2015 | Anderson et al. |
| 9,046,227 B2 | 6/2015 | David et al. |
| 9,078,306 B2 | 7/2015 | Mans et al. |
| 9,119,240 B2 | 8/2015 | Nagazoe |
| 9,173,276 B2 | 10/2015 | Van Der Veen et al. |
| 9,257,059 B2 | 2/2016 | Raksha et al. |
| 9,283,292 B2 | 3/2016 | Kretschmann |
| 9,313,860 B2 | 4/2016 | Wingren |
| 9,323,894 B2 | 4/2016 | Kiani |
| 9,333,274 B2 | 5/2016 | Peterson et al. |
| 9,368,695 B2 | 6/2016 | David et al. |
| 9,410,664 B2 | 8/2016 | Krames et al. |
| 9,420,671 B1 | 8/2016 | Sugimoto et al. |
| 9,433,051 B2 | 8/2016 | Snijder et al. |
| 9,439,271 B2 | 9/2016 | Ku et al. |
| 9,439,989 B2 | 9/2016 | Lalicki et al. |
| 9,492,576 B1 | 11/2016 | Cudak et al. |
| 9,581,310 B2 | 2/2017 | Wu et al. |
| 9,623,138 B2 | 4/2017 | Pagan et al. |
| 9,625,137 B2 | 4/2017 | Li et al. |
| 9,681,510 B2 | 6/2017 | van De Ven |
| 10,806,812 B2 | 10/2020 | Barron et al. |
| 2002/0074559 A1 | 6/2002 | Dowling et al. |
| 2002/0122743 A1 | 9/2002 | Huang |
| 2003/0009158 A1 | 1/2003 | Perricone |
| 2003/0019222 A1 | 1/2003 | Takahashi et al. |
| 2003/0023284 A1 | 1/2003 | Gartstein et al. |
| 2003/0124023 A1 | 7/2003 | Burgess et al. |
| 2003/0178632 A1 | 9/2003 | Hohn et al. |
| 2003/0207644 A1* | 11/2003 | Green ............... A61L 2/10 445/24 |
| 2003/0222578 A1 | 12/2003 | Cok |
| 2003/0231485 A1 | 12/2003 | Chien |
| 2004/0008523 A1 | 1/2004 | Butler |
| 2004/0010299 A1 | 1/2004 | Tolkoff et al. |
| 2004/0024431 A1 | 2/2004 | Carlet |
| 2004/0039242 A1 | 2/2004 | Tolkoff et al. |
| 2004/0047142 A1 | 3/2004 | Goslee |
| 2004/0147984 A1 | 7/2004 | Altshuler et al. |
| 2004/0147986 A1 | 7/2004 | Baumgardner et al. |
| 2004/0158541 A1 | 8/2004 | Notarianni et al. |
| 2004/0159039 A1 | 8/2004 | Yates et al. |
| 2004/0162596 A1 | 8/2004 | Altshuler et al. |
| 2004/0230259 A1 | 11/2004 | Di Matteo |
| 2004/0262595 A1 | 12/2004 | Mears et al. |
| 2004/0266546 A1 | 12/2004 | Huang |
| 2005/0055070 A1 | 3/2005 | Jones et al. |
| 2005/0104059 A1 | 5/2005 | Friedman et al. |
| 2005/0107849 A1 | 5/2005 | Altshuler et al. |
| 2005/0107853 A1 | 5/2005 | Krespi et al. |
| 2005/0159795 A1 | 7/2005 | Savage et al. |
| 2005/0207159 A1 | 9/2005 | Maxik |
| 2005/0212397 A1 | 9/2005 | Murazaki et al. |
| 2005/0253533 A1 | 11/2005 | Lys et al. |
| 2005/0267233 A1 | 12/2005 | Joshi |
| 2006/0006678 A1 | 1/2006 | Herron |
| 2006/0009822 A1 | 1/2006 | Savage et al. |
| 2006/0022582 A1 | 2/2006 | Radkov |
| 2006/0071589 A1 | 4/2006 | Radkov |
| 2006/0085052 A1 | 4/2006 | Feuerstein et al. |
| 2006/0138435 A1 | 6/2006 | Tarsa et al. |
| 2006/0186377 A1 | 8/2006 | Takahashi et al. |
| 2006/0230576 A1 | 10/2006 | Meine |
| 2006/0247741 A1 | 11/2006 | Hsu et al. |
| 2006/0262545 A1 | 11/2006 | Piepgras et al. |
| 2007/0023710 A1 | 2/2007 | Tom et al. |
| 2007/0061050 A1 | 3/2007 | Hoffknecht |
| 2007/0115665 A1 | 5/2007 | Mueller et al. |
| 2007/0164232 A1 | 7/2007 | Rolleri et al. |
| 2007/0208395 A1 | 9/2007 | Leclerc et al. |
| 2007/0258851 A1 | 11/2007 | Fogg et al. |
| 2008/0008620 A1 | 1/2008 | Alexiadis |
| 2008/0015560 A1 | 1/2008 | Gowda et al. |
| 2008/0091250 A1 | 4/2008 | Powell |
| 2008/0151533 A1 | 6/2008 | Genova |
| 2008/0278927 A1 | 11/2008 | Li et al. |
| 2008/0305004 A1 | 12/2008 | Anderson et al. |
| 2008/0307818 A1 | 12/2008 | Min et al. |
| 2009/0018621 A1 | 1/2009 | Vogler et al. |
| 2009/0034236 A1 | 2/2009 | Reuben |
| 2009/0076115 A1 | 3/2009 | Wharton et al. |
| 2009/0154167 A1 | 6/2009 | Lin |
| 2009/0231832 A1 | 9/2009 | Zukauskas et al. |
| 2009/0262515 A1 | 10/2009 | Lee et al. |
| 2009/0285727 A1 | 11/2009 | Levy |
| 2009/0314308 A1 | 12/2009 | Kim et al. |
| 2010/0001648 A1 | 1/2010 | De Clercq et al. |
| 2010/0027259 A1 | 2/2010 | Simon et al. |
| 2010/0071257 A1 | 3/2010 | Tsai |
| 2010/0090935 A1 | 4/2010 | Tseng et al. |
| 2010/0102252 A1 | 4/2010 | Harmon et al. |

(56) References Cited

U.S. PATENT DOCUMENTS

| | | |
|---|---|---|
| 2010/0107991 A1 | 5/2010 | Elrod et al. |
| 2010/0121420 A1 | 5/2010 | Fiset et al. |
| 2010/0148083 A1 | 6/2010 | Brown et al. |
| 2010/0179469 A1 | 7/2010 | Hammond et al. |
| 2010/0232135 A1 | 9/2010 | Munehiro et al. |
| 2010/0246169 A1 | 9/2010 | Anderson et al. |
| 2011/0063835 A1 | 3/2011 | Rivas et al. |
| 2011/0084614 A1 | 4/2011 | Eisele et al. |
| 2011/0256019 A1 | 10/2011 | Gruen et al. |
| 2011/0316025 A1 | 12/2011 | Kuzuhara et al. |
| 2012/0014538 A1 | 1/2012 | Bozkurt et al. |
| 2012/0025717 A1 | 2/2012 | Klusmann et al. |
| 2012/0043552 A1 | 2/2012 | David et al. |
| 2012/0161170 A1 | 6/2012 | Dubuc et al. |
| 2012/0199005 A1 | 8/2012 | Koji et al. |
| 2012/0273340 A1 | 11/2012 | Felix |
| 2012/0280147 A1 | 11/2012 | Douglas |
| 2012/0281408 A1 | 11/2012 | Owen et al. |
| 2012/0315626 A1 | 12/2012 | Nishikawa et al. |
| 2012/0320607 A1 | 12/2012 | Kinomoto et al. |
| 2013/0010460 A1 | 1/2013 | Peil et al. |
| 2013/0045132 A1 | 2/2013 | Tumanov |
| 2013/0077299 A1 | 3/2013 | Hussell et al. |
| 2013/0181246 A1 | 7/2013 | Wu |
| 2013/0200279 A1 | 8/2013 | Chuang |
| 2013/0298445 A1 | 11/2013 | Aoki et al. |
| 2013/0313516 A1 | 11/2013 | David et al. |
| 2013/0313546 A1 | 11/2013 | Yu |
| 2013/0323375 A1 | 12/2013 | Takahashi et al. |
| 2014/0043810 A1 | 2/2014 | Jo et al. |
| 2014/0061509 A1 | 3/2014 | Shur et al. |
| 2014/0209944 A1 | 7/2014 | Kim et al. |
| 2014/0225137 A1 | 8/2014 | Krames et al. |
| 2014/0254131 A1 | 9/2014 | Osinski et al. |
| 2014/0265868 A1 | 9/2014 | Morrisseau |
| 2014/0301062 A1 | 10/2014 | David et al. |
| 2014/0328046 A1 | 11/2014 | Aanegola et al. |
| 2014/0334137 A1 | 11/2014 | Hasenoehrl et al. |
| 2014/0362523 A1 | 12/2014 | Degner et al. |
| 2015/0049459 A1 | 2/2015 | Peeters et al. |
| 2015/0062892 A1 | 3/2015 | Krames et al. |
| 2015/0068292 A1 | 3/2015 | Su et al. |
| 2015/0086420 A1 | 3/2015 | Trapani |
| 2015/0129781 A1 | 5/2015 | Kretschmann |
| 2015/0148734 A1 | 5/2015 | Fewkes et al. |
| 2015/0150233 A1 | 6/2015 | Dykstra |
| 2015/0182646 A1 | 7/2015 | Anderson et al. |
| 2015/0219308 A1 | 8/2015 | Dross et al. |
| 2015/0233536 A1 | 8/2015 | Krames et al. |
| 2015/0273093 A1 | 10/2015 | Holub et al. |
| 2016/0000950 A1 | 1/2016 | Won |
| 2016/0000953 A1 | 1/2016 | Bettles et al. |
| 2016/0015840 A1 | 1/2016 | Gordon |
| 2016/0030609 A1 | 2/2016 | Peterson et al. |
| 2016/0030610 A1 | 2/2016 | Peterson et al. |
| 2016/0091172 A1 | 3/2016 | Wu et al. |
| 2016/0114067 A1 | 4/2016 | Dobrinsky et al. |
| 2016/0114186 A1 | 4/2016 | Dobrinsky et al. |
| 2016/0137528 A1 | 5/2016 | Wipprich |
| 2016/0168384 A1* | 6/2016 | Guidolin ............... A61L 2/084 250/436 |
| 2016/0249436 A1 | 8/2016 | Inskeep |
| 2016/0271280 A1 | 9/2016 | Liao et al. |
| 2016/0271281 A1 | 9/2016 | Clynne et al. |
| 2016/0273717 A1 | 9/2016 | Krames et al. |
| 2016/0276550 A1 | 9/2016 | David et al. |
| 2016/0324996 A1 | 11/2016 | Bilenko et al. |
| 2016/0345569 A1 | 12/2016 | Freudenberg et al. |
| 2016/0346565 A1 | 12/2016 | Rhodes et al. |
| 2016/0349179 A1 | 12/2016 | Rochette et al. |
| 2016/0354502 A1 | 12/2016 | Simmons et al. |
| 2016/0366745 A1 | 12/2016 | Hikmet et al. |
| 2016/0375161 A1 | 12/2016 | Hawkins et al. |
| 2016/0375162 A1 | 12/2016 | Marry et al. |
| 2016/0375163 A1 | 12/2016 | Hawkins et al. |
| 2017/0014538 A1 | 1/2017 | Rantala |
| 2017/0030555 A1 | 2/2017 | Lalicki et al. |
| 2017/0081874 A1 | 3/2017 | Daniels |
| 2017/0094960 A1 | 4/2017 | Sasaki et al. |
| 2017/0100494 A1 | 4/2017 | Dobrinsky et al. |
| 2017/0100607 A1 | 4/2017 | Pan et al. |
| 2017/0281812 A1 | 10/2017 | Dobrinsky et al. |
| 2017/0368210 A1 | 12/2017 | David et al. |
| 2018/0043044 A1 | 2/2018 | Hachiya et al. |
| 2018/0113066 A1 | 4/2018 | Freitag et al. |
| 2018/0117189 A1 | 5/2018 | Yadav et al. |
| 2018/0117190 A1 | 5/2018 | Bailey |
| 2018/0117193 A1 | 5/2018 | Yadav et al. |
| 2018/0117194 A1 | 5/2018 | Dobrinsky et al. |
| 2018/0124883 A1 | 5/2018 | Bailey |
| 2018/0139817 A1 | 5/2018 | Yamakawa et al. |
| 2018/0180226 A1 | 6/2018 | Van Bommel et al. |
| 2018/0185533 A1 | 7/2018 | Lalicki et al. |
| 2018/0190625 A1 | 7/2018 | Steckel et al. |
| 2018/0280723 A1 | 10/2018 | Enwemeka et al. |
| 2018/0311386 A1* | 11/2018 | Hawkins ............... F21V 5/04 |
| 2019/0070323 A1* | 3/2019 | Atreya ............... A61L 2/0052 |
| 2019/0256379 A1* | 8/2019 | Kato ............... B01J 19/2415 |
| 2019/0368936 A1 | 12/2019 | Xu et al. |
| 2019/0371978 A1* | 12/2019 | Iwasa ............... H01L 33/504 |
| 2020/0078482 A1* | 3/2020 | Yoon ............... A61N 5/0624 |
| 2020/0405893 A1* | 12/2020 | Barron ............... A61L 2/084 |

FOREIGN PATENT DOCUMENTS

| | | |
|---|---|---|
| CN | 201423033 Y | 3/2010 |
| CN | 102213382 A | 10/2011 |
| CN | 103227225 A | 7/2013 |
| CN | 105304801 A | 2/2016 |
| CN | 105339094 A | 2/2016 |
| CN | 105449081 A | 3/2016 |
| CN | 205360038 U | 7/2016 |
| CN | 106937461 A | 7/2017 |
| CN | 607575849 A | 1/2018 |
| DE | 102011001097 A1 | 9/2012 |
| DE | 102015207999 A1 | 11/2016 |
| DE | 102016009175 A1 | 2/2017 |
| EP | 0306301 A1 | 3/1989 |
| EP | 1693016 A1 | 8/2006 |
| EP | 1887298 A1 | 2/2008 |
| EP | 1943880 B1 | 4/2013 |
| FR | 2773715 A1 | 7/1999 |
| JP | 2003-332620 A | 11/2003 |
| JP | 2003339845 A | 12/2003 |
| JP | 2004261595 A | 9/2004 |
| JP | 2004275927 A | 10/2004 |
| JP | 2007511279 A | 5/2007 |
| JP | 2008-004948 A | 1/2008 |
| JP | 2009-004351 A | 1/2009 |
| JP | 2011-513996 A | 4/2011 |
| JP | 2013-045896 A | 3/2013 |
| JP | 2013-093311 A | 5/2013 |
| JP | 2015-015106 A | 1/2015 |
| JP | 2015-035373 A | 2/2015 |
| JP | 2015174026 A | 10/2015 |
| KR | 20130096965 A | 9/2013 |
| KR | 101526261 B1 | 6/2015 |
| KR | 20160021100 A | 2/2016 |
| KR | 101648216 B1 | 8/2016 |
| KR | 20160127469 A | 11/2016 |
| KR | 101799538 B1 | 11/2017 |
| TW | M268106 U | 6/2005 |
| TW | 201412240 A | 4/2014 |
| TW | 201604490 A | 2/2016 |
| TW | 201611849 A | 4/2016 |
| TW | M530654 U | 10/2016 |
| TW | 201711707 A | 4/2017 |
| TW | 201831977 A | 9/2018 |
| TW | 201936226 A | 9/2019 |
| WO | 0114012 A1 | 3/2001 |
| WO | 03037504 A1 | 5/2003 |
| WO | 2003035118 A2 | 5/2003 |
| WO | 03063902 A2 | 8/2003 |
| WO | 03084601 A2 | 10/2003 |

(56) References Cited

FOREIGN PATENT DOCUMENTS

| WO | 03089063 | A1 | 10/2003 | | |
|---|---|---|---|---|---|
| WO | 2004033028 | A2 | 4/2004 | | |
| WO | 2005048811 | A2 | 6/2005 | | |
| WO | 2005049138 | A1 | 6/2005 | | |
| WO | 2006023100 | A1 | 3/2006 | | |
| WO | 2006100303 | A2 | 9/2006 | | |
| WO | 2006126482 | A1 | 11/2006 | | |
| WO | 2007012875 | A1 | 2/2007 | | |
| WO | 2007035907 | A2 | 3/2007 | | |
| WO | 2008071206 | A1 | 6/2008 | | |
| WO | 2009056838 | A1 | 5/2009 | | |
| WO | 2010110652 | A1 | 9/2010 | | |
| WO | 2015066099 | A2 | 5/2015 | | |
| WO | 2015189112 | A1 | 12/2015 | | |
| WO | 2016019029 | A1 | 2/2016 | | |
| WO | 2016068285 | A1 | 5/2016 | | |
| WO | 2016209632 | A1 | 12/2016 | | |
| WO | 12017009534 | A1 | 1/2017 | | |
| WO | WO-2017179082 | A1 | * 10/2017 | ............ | A61L 2/084 |
| WO | 2017205578 | A1 | 11/2017 | | |
| WO | 2019108432 | A1 | 6/2019 | | |

OTHER PUBLICATIONS

Tomb et al., Assessment of the potential for resistance to antimicrobial violet-blue light in *Staphylococcus aureus*, 2017, Antimicrobial Resistance and Infection Control, 6:100 (Year: 2017).*
Gillespie et al., Development of an antimicrobial blended white LED system containing pulsed 405nm LEDs for decontamination applications, Mar. 14, 2017, Proc. SPIE 10056 (Year: 2017).*
Apr. 14, 2020—(TW) 2nd Office Action—App 107143577 (w/translation).
Jul. 23, 2020—(TW) Office Action w/TR—TW 108148627.
Jul. 6, 2020—(WO) ISR & WO—App PCT/US2019/068799.
Jun. 1, 2020—(GB) Examiner's Report—App GB1802648.4.
Jun. 18, 2020—(WO) IPRP & WO—App PCT/US2018/061859.
May 12, 2020—(JP) Final Office Action—JP 2018-525520.
Jul. 28, 2020—(TW) Office Action 3 w/TR—TW 107143577.
Nov. 30, 2020—(GB) Intent to Grant—GB1802648.4.
Nov. 6, 2020—(TW) Office Action w/Tr.—TW 108146777.
Dec. 2, 2020—(TW) Rejection Decision—App 108111242 (Eng Trans).
Sep. 29, 2020—(WO) ISR & WO—App PCT/US2020/046504.
Nov. 23, 2020—(WO) ISR & WO—App PCT/US2020/051254.
Maclean et al., "Inactivation of Bacterial Pathogens following Exposure to Light from a 405-Nanometer Light-Emitting Diode Array," Applied and Environmental Microbiology, vol. 75, No. 7, Apr. 2009, pp. 1932-1937, 6 pages.
Gillespie et al., "Development of an antimicrobial blended white LED system containing pulsed 405nm LEDs for decontamination applications," Progress in Biomedical Optics and Imaging, SPIE—International Society for Optical Engineering, Bellingham, WA, vol. 10056, Mar. 14, 2017, pp. 100560Y-100560Y, XP060084045, whole document.
Aug. 31, 2021—(CN) Office Action—CN 201980033309.1.
Sep. 21, 2021—(JP) Office Action—2020-154129.
Oct. 21, 2021—(TW) Office Action—TW 109132488 w/Trn.
Jul. 21, 2021—(TW) Office Action—TW 108148627.
Dai et al., "Blue light for infectious diseases: Propionibacterium acnes, Helicobacter pylori, and beyond?," Drug Resist Update, 15(4): 223-236 {Aug. 2012), 18 pages.
Halstead et al., "The antibacterial activity of blue light against nosocomial wound pathogens growing planktonically and as mature biofilms," Appl. Environ. Microbial., vol. 82, No. 13, Jul. 2016, pp. 4006-4016, 11 pages, retrieved from: https://aem.asm.org/content/aem/82/13/4006.full.pdf.
R.S. McDonald et al., "405 nm Light Exposure of Osteoblasts and Inactivation of Bacterial Isolates From Arthroplasty Patients: Potential for New Disinfection Applications?," European Cells and Materials vol. 25, (2013), pp. 204-214., 12 pages.

Tomb et al., "Inactivation of Streptomyces phage C31 by 405 nm light," Bacteriophage, 4:3, Jul. 2014, retrieved from: http://dx.doi.org/10.4161/bact.32129, 7 pages.
Tsukada et al., "Bactericidal Action of Photo-Irradiated Aqueous Extracts from the Residue of Crushed Grapes from Winemaking," Biocontrol Science, vol. 21, No. 2, (2016), pp. 113-121, retrieved from: https://www.researchgate.net/publication/304628914., 10 pages.
Dec. 8, 2016—(WO) ISR & WO—App PCT/US2016/036704 (Kenall Manufacturing Company).
LEDs Magazine, "Lumination Vio LED combines 405 nm chip with new phosphors," retrieved from the Internet on Apr. 20, 2017 at: http://www.leds.magazine.com/articles/2007/06/lumination-vio-led-combines-405-nm-chip-with-new-phosphors.html, Published Jun. 14, 2007, 2 pages.
LEDs Magazine, "ANSI evaluates revisions to SSL chromaticity standard," retrieved from the Internet on Apr. 20, 2017 at: http://www.ledsmagazine.com/articles/2011/07/ansi-evaluates-revisions-to-ssl-chromaticity-standard-magazine.html, Published Jul. 18, 2011, 4 pages.
LEDs Magazine, "ANSI works to update the solid-state lighting standard for chromaticity," retrieved from the Internet on Apr. 20, 2017 at: http://www.ledsmagazine.com/articles/print/volume-12/issue-2/features/standards/ansi-works-to-update-the-ssl-chromaticity-standard.html, Published Feb. 23, 2015, 5 pages.
LEDs Magazine, "ANSI continues advancements on SSL chromaticity standard," retrieved from the Internet on Apr. 20, 2017 at: http://www.ledsmagazine.com/articles/print/volume12/issue-11/features/standards/ansi-continues-advancements-on-ssl-chromaticity-standard.html, Published Dec. 8, 2015, 6 pages.
Soraa, "PAR30L," retrieved from the Internet on Apr. 20, 2017 at: http://www_soraa.com/products/22-PAR30L, 6 pages.
Soraa, "PAR30L 18.5W," retrieved from the Internet on Apr. 20, 2017 at: http://www.soraa.com/products, 5 pages.
Bache et al., "Clinical studies of the High-Intensity Narrow-Spectrum light Environmental Decontamination System (HINS-light EDS), for continuous disinfection in the burn unit inpatient and outpatient settings," Burns 38 (2012), pp. 69-76, 8 pages.
Oct. 20, 2016—(WO) ISR & WO—App PCT/US2016/44634.
Color Phenomena, "CIE-1931 Chromaticity Diagram," last updated Aug. 22, 2013, retrieved from www.color-theory-phenomena.nl/10.02.htm on Jan. 20, 2016, 3 pages.
Nov. 2, 2015—(WO) WO & ISR—App PCT/US2015/042678.
Yu, J. et al., "Efficient Visible-Light-Induced Photocatalytic Disinfection on Sulfur-Doped Nanocrystalline Titania," Environ. Sic. Technol., 39, 2005, pp. 1175-1179, 5 pages.
Demidova, T. et al., "Photodynamic Therapy Targeted to Pathogens," International Journal of Immunipathology and Pharmacology, 17(3), pp. 245-254, 10 pages.
Ashkenazi, H. et al., "Eradication of Propionibacterium acnes by its endogenic porphyrins after illumination with high Intensity blue light," FEMS Immunology and Medical Microbiology, 35, pp. 17-24, 8 pages.
Elman, M. et al., "The Effective Treatment of Acne Vulgaris by a High-intensity, Narrow Band 405-420 nm Light Source," Cosmetic & Laser Ther, 5, pp. 111-116, 6 pages.
Sikora, A. et al., "Lethality of visable light for *Escherichia colihemH* 1 mutants influence of defects in DNA repair," DNA Repair 2, pp. 61-71, 11 pages.
Huffman, D. et al., "Inactivation of Bacteria, Virus and Cryptospordium by a Point-of-use Device Using Pulsed Broad Spectrum White Light," Wat. Res. 34(9), pp. 2491-2498, 8 pages.
Papageorgiou, P. et al., "Phototherapy with Blue (415 nm) and Red (660 nm) Light in the Treatment of Acne Vulgaris," British Journal of Dermatology, 2000, pp. 973-978, 6 pages.
Burchard, R. et al., "Action Spectrum for Carotenogenesis in Myxococcus xanthus," Journal of Bateriology, 97(3), 1969, pp. 1165-1168, 4 pages.
Wainwright, "Photobacterial activity of phenothiazinium dyes against methicillin-resistant strains of *Staphylococcus aureus*," Oxford University Press Journals, retrieved from: http://dx.doi.org/10.1111/j.1574-6968.1998.tb12908.x on Jul. 23, 2015, 8 pages.

(56) References Cited

OTHER PUBLICATIONS

Yoshimura et al., "Antimicrobial effects of phototherapy and photochemotherapy in vivo and in vitro," British Journal of Dermatology, 1996, 135: 528-532, 6 pages.
Wilson et al., "Killing of methicillin-resistant *Staphylococcus aureus* by low-power laser light," J. Med, Microbial., vol. 42 (1995), pp. 62-66, 5 pages.
Kawada et al., "Acne Phototherapy with a high-intensity, enhanced, narrow-band, blue light source: an open study and In vitro investigation," Journal of Dermatological Science 30 (2002) pp. 129-135, 7 pages.
Maclean et al., "High-intensity narrow-spectrum light inactivation and wavelength sensitivity of *Staphylococcus auresu*," FEMS Microbial. Lett., vol. 285 (2008) pp. 227-232, 6 pages.
Reed, "The History of Ultraviolet Germicidal Irradiation for Air Disinfection," Public Health Reports, Jan.-Feb. 2010, vol. 125, 13 pages.
Ward, "Experiments on the Action of Light on Bacillus anthracis," Received Dec. 15, 1892, 10 pages.
Hamblin et al., "Helicobacter pylori Accumulates Photoactive Porphyrins and Is Killed by Visable Light," Antimicrobial Agents and Chemotherapy, Jul. 2005, pp. 2822-2827, 6 pages.
Dai et al., "Blue Light Rescues Mice from Potentially Fatal Pseudomonas aeruginosa Burn Infection: Efficacy, Safety, and Mechanism of Action," Antimicrobial Agents and Chemotherapy, Mar. 2013, vol. 57{3}, pp. 1238-1245, 8 pages.
Holzman, "405-nm Light Proves Potent at Decontaminating Bacterial Pathogens," retrieved from: http://forms.asm.org/microbe/index.asp?bid=64254 on Aug. 6, 2015, 34 pages.
Guffey et al., "In Vitro Bactericidal Effects of 405-nm and 470-nm Blue Light," Photomedicine and Laser Surgery, vol. 24, No. 6, retrieved from: https://www.liebertpub.com/doi/abs/10.1089/pho.2006.24.684 on Mar. 23, 2018, abstract only provided, 2 pages.
Kristoff et al., "Loss of photoreversibility for UV mutation in *E. coli* using 405 nm or near-US challenge," Mutat Res., May 1983, 109{2}: 143-153, 2 pages, abstract only provided.
Turner et al., "Comparative Mutagenesis and Interaction Between Near-Ultraviolet {313- to 405-nm) and Far-Ultraviolet 254-nm) Radiation in *Escherichia coli* Strains with Differeing Repair Capabilities," Journal of Bacteriology, vol. 147, No. 2, Aug. 1981, pp. 410-417, 8 pages.
Knowles et al., "Near-Ultraviolet Mutagenesis in Superoxide Dismutase-deficient Strains of *Escherichia coli*," Environmental Health Perspectives, vol. 102(1), Jan. 1994, pp. 88-94, 7 pages.
Jagger, "Photoreactivation and Photoprotection," Photochemistry and Photobiology, vol. 3, Issue 4, Dec. 1964, retrieved from: https://onlinelibrary.wiley.com/doi/abs/10.1111/j.1751-1097.1964.tb08166.x on Mar. 23, 2018, 4 pages, abstract only provided.
Chukuka et al., Visible 405 nm SLD light photo-destroys metchicillin-resistant *Staphylococcus aureus* {MRSA) in vitro, Lasers in Surgery and Medicine, vol. 40, Issue 10, Dec. 8, 2008, retrieved from: https:/onlinelibrary.wiley.com/doi/abs/10.1002/lsm.20724 on Mar. 23, 2018, 4 pages, abstract only provided.
Bek-Thomsen, M., "Acne is Not Associated with Yet-Uncultured Bacteria," J. Clinical Microbial., 2008, 46{10), 9 pages.
Harrison, A.P., "Survival of Bacteria," Annu. Rev. Microbial, 1967, p. 143, vol. 21, 1 page.
Feuerstein et al., "Phototoxic Effect of Visible Light on Porphyromonas gingivalis and Fusobacterium nucleatum: An In Vitro Study," Photochemistry and Photobiology, vol. 80, Issue 3, Apr. 30, 2007, retrieved from: https://onlinelibrary.wiley.com/doi/abs/10.1111/j.1751-1097.2004.tb00106.x on Mar. 23, 2018, abstract only, 4 pages.
Pochi, P.E., "Acne: Androgens and microbiology," Drug Dev, Res., 1988, val. 13, 4 pages, abstract only provided.
Burkhart, C. G. et al., "Acne: a review of immunologic and microbiologic factors," Postgraduate Medical Journal, 1999, vol. 75, pp. 328-331, 5 pages.
Jappe, U., "Pathological mechanisms of acne with special emphasis on Propionibacterium acnes and related therapy," Acta Dermato-Venereologica, 2003, vol. 83, pp. 241-248, 8 pages.
Burkhart, C. N. et al., "Assessment of etiologic agents in acne pathogenesis," Skinmed, 2003, vol. 2, No. 4, pp. 222-228, 7 pages.
Tong, Y., et al. "Population study of atmospheric bacteria at the Fengtai district of Beijing on two representative days," Aerobiologica, 1993, vol. 9, 1 page, Abstract only provided.
Tong, Y. et al., "Solar radiation is shown to select for pigmented bacteria in the ambient outdoor atmosphere," Photochemistry and Photobiology, 1997, val. 65, No. 1, pp. 103-106, 4 pages.
Marshall, J. H., et al., "Pigments of *Staphylococcus au reus*, a series of triterpenoid carotenoids," J. Bacteriology, 1981, vol. 147, No. 3, pp. 900-913, 14 pages.
Pelz, A. et al., "Structure and Biosythesis of Staphyloxanthin from *Staphylococcus aureus*," Journal of Biological Chemistry, Sep. 16, 2005, 9 pages.
Sakai, K., et al., "Search Method for inhibitors of staphyloxanthin production by methicillin-resistant *Staphylococcus aureus*," Biol. Pharm. Bull., 2012, vol. 35, No. 1, pp. 48-53, 6 pages.
Clauditz, A. et al., "Staphyloxanthin plays a role in the fitness of *Staphylococcus aureus* and its ability to cope with oxidative stress," Infection and Immunity, 2006, vol. 74, No. 8, 7 pages.
Feng Chyi Duh et al., "Innovative Design of an Anti-bacterial Shopping Cart Attachment", Journal of Multidisciplinary Engineering Science and Technology (JMEST), Oct. 10, 2015, vol. 2 Issue 10, pp. 2806-2810, http://www.jmest.org/wp-content/uploads/JMESTN42351112.pdf, 5 pages.
Drew Prindle, "This UV-Emitting Door Handle Neutralizes Bacteria, Helps Fight the Spread of Disease", Digital Trends, Jun. 19, 2015, https://www.digitaltrends.com/cool-tech/uv-door-handle-kills-germs/, 11 pages.
Jun. 29, 2018—(DE) Office Action—App 112016003453.9.
Kundrapu et al. "Daily disinfection of high touch surfaces in isolation rooms to reduce contamination of healthcare workers' hands". Joumal of Infection Control and Hospital Epidemiology; vol. 33, No. 10, pp. 1039-1042, published Oct. 2012, 6 pages.
Sofia Pitt and Andy Rothman, "Bright idea aims to minimize hospital-acquired infections", CNBC News website, published on Dec. 9, 2014 and retrieved from website: https://www.cnbc.com/2014/12/09/bright-idea-aims-to-minimize-hospital-acquired-infections.html. 5 pages.
Sarah Ward, "LED Retrofit Health ROI? See VitalVio", Poplar Network website, published on Aug. 13, 2014 and retrieved from website: https://www.poplarnetwork.com/news/led-retrofit-health-roi-see-vitalvio, 6 pages.
Mar. 6, 2018—(WO) ISR & WO—App PCT/US2017/068749.
Apr. 16, 2018—(WO) ISR & WO—App PCT/US2017/068755.
Wang, Shun-Chung, et al.; "High-Power-Factor Electronic Ballast With Intelligent Energy-Saving Control for Ultraviolet Drinking-Waler Treatment Systems"; IEEE Transactions on Industrial Electronics; vol. 55; Issue 1; Dale of Publication Jan. 4, 2008; Publisher IEEE, 4 pages.
Berezow Alex, How to Kill Insects With Visible Light, Real Clear Science, Jan. 11, 2015, pp. 1-4<https://www.realclearscience.com/journal_club/2015/01/12/how_to_kill_insects_with_visible_light_109021.html>, 4 pages.
Hori Masatoshi et al., Lethal Effects of Short-Wavelength Visible Light on Insects, Scientific Reports, Dec. 9, 2014, pp. 1-6, Graduate School of Agricultural Science, Tohoku University, Sendai, Japan<https://www.semanticscholar.org/paper/Lethal-effects-of-short-wavelength-visible-light-o-Hori-Shibuya/2c11cb3f70a059a051d8ed02fff0e8a9b7a4c4d4>, 6 pages.
Master Blaster, Tohoku University Team Discovers Blue Light is Effect at Killing Insects, Sora News 24, Dec. 12, 2014, pp. 1-5, Japan, <https://en.rocketnews24.com/2014/12/12/tohoku-university-team-discovers-blue-light-is-effective-at-killing-insects/>, 5 pages.
Dornob, "Healthy Handle: Self-Sanitizing UV Door Knob Kills Germs", Dornob.com, Dec. 5, 2018, pp. 1-6, https://dornob.com/healthy-handle-self-sanitizing-uv-door-knob-kills-germs/, 6 pages.
Kickstarter, "Orb, The World's First Germ-Killing Blue/UV Light Ball", Dec. 10, 2018, pp. 1-10, <https://www.kickstarter.com/projects/572050089078660/orbtm-the-worlds-first-germ-killing-uv-light-ball>, 10 pages.
NuTone, "QTNLEDB LunAura Collection 110 CFM Fan, Light, LED Nightlight, with Tinted Light Panel, Energy Star® Certified

(56) References Cited

OTHER PUBLICATIONS

Ventilation Fans", Dec. 11, 2018, p. 1, http://www.nutone.com/products/product/a6da75af-8449-4d4d-8195-7011ce977809, 1 page.
NuTone, "NuTone Bath and Ventilation Fans", Dec. 11, 2018, pp. 1-2, http://www.nutone.com/products/filter/qt-series-fanlights-25a05450-d47b-4ab8-9992-f8c2cd3f7b90, 2 pages.
NuTone, "Ultra Pro™ Series Single-Speed Fans and Fan/Lights", Dec. 11, 2018, p. 1, http://www.hutone.com/products/filter/ultra-pro-series-fanlights-eb590f89-dca2-40e7-af39-06e4cccb96ca, 1 page.
Nov. 27, 2018—(JP) Office Action—JP 2018-525520.
Jan. 4, 2019—(TW) Office Action—App 104124977.
Feb. 11, 2019—(WO) ISR—App PCT/US2018/061859.
Feb. 28, 2019—(WO) ISR—App PCT/US2018/061843.
Feb. 28, 2019—(WO) ISR & WO—App PCT/US2018/061856.
Apr. 15, 2019—(CA) Examiner's Report—App 2,993,825.
Absorption and Fluorescence Spectroscopy of Tetraphenylporphyrins and Metallo-Tetraphenylporphyrin, article, 2005, 11 pp., Atomic, Molecular and Supramolecular Studies.
Dayer, et al., Band Assignment in Hemoglobin Porphyrin Ring Spectrum: Using Four- Orbital Model of Gouterman, article, Sep. 8, 2009, Protein & Peptide Letters, 2010, vol. 17, No. 4, Department of Biology, Faculty of Sciences, Shahid Chamran University of Ahvaz, Tehran, Iran, 7 pages.
Ayat M. Ali, Effect of MRSA Irradiation by 632, 532, and 405 nm (Red, Blue, and Green) Diode Lasers on Antibiotic Susceptibility Tests, Article, Jun. 2007, 7 pp, vol. 59, No. 2 , 2017, J Fac Med Baghdad.
Nussbaum, et al., Effects of 630-, 660-, 810-, and 905-nm Laser Irradiation, Delivering Radiant Exposure of 1-50 J/cm2 on Three Species of Bacteria in Vitro, journal, 2002, vol. 20, No. 6, 2002, Journal of Clinical LaserMedicine & Surgery, Canada, 9 pages.
Kim, et al., In Vitro Bactericidal Effects of 625, 525, and 425nm Wavelength (Red, Green, and Blue) Light-Emitting Diode Irradiation, article, 2013, 9 pp., vol. 31, No. 11, 2013, Department of Oral Pathology Medical Research Center for Biomineralization Disorders School of Dentistry Dental Science Research Institute, Korea, 9 pages.
Rita Giovannetti, The Use of Spectrophotometry UV-Vis for the Study of Porphyrins, article, 2012, 23 pp., InTech Europe, Croatia.
Josefsen, et al., Unique Diagnostic and Therapeutic Roles of Porphyrins and Phthalocyanines in Photodynamic Therapy, Imaging and Theranostics, article, Oct. 4, 2012, 51 pp., 2012; 2(9):916-966. doi: 10.7150/thno.4571, Ivyspring International Publisher, Department of Chemistry, The University of Hull, Kingston-Upon-Hull, HU6 7RX, U. K., 51 pages.
Jul. 8, 2019—(WO) ISR & WO—App PCT/US2019/024593.
Nov. 5, 2019—(JP) Final Office Action—JP 2018-525520.
Oct. 9, 2019—(CN) Office Action—CN 201680048598.9.
Oct. 1, 2019—(KR) Office Action—App 10-2018-7005077—Eng Tran.
Apr. 15, 2019—(CA) Office Action—App 2,993,825.
Nov. 20, 2019—(CA) Examiner's Report—App 2,993,825.
Dec. 26, 2019—(TW) Office Action and Search Report—App 107143161.
Dec. 27, 2019—(TW) Office Action and Search Report—App 108111242.
Sep. 6, 2019—(TW) Office Action—App 107143162.
Sep. 20, 2019—(TW) Office Action—App 107143577.
Mar. 18, 2020—(WO) ISR & WO—App PCT/US2019/068799.
Oct. 31, 2008—(WO) ISR & WO—App PCT/GB2008/003679 (Univ Strathclyde).
May 4, 2010—(WO) IPRP—App PCT/GB2008/003679 (Univ Strathclyde).
Apr. 3, 2020—(WO) ISR & WO—App PCT/US2019/67444.

\* cited by examiner

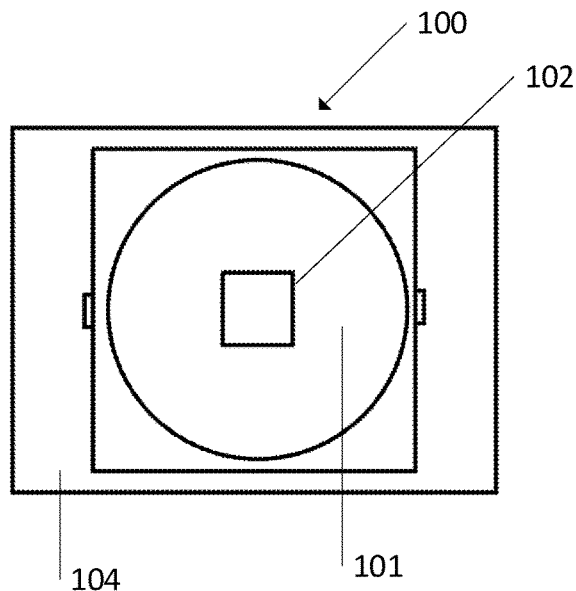
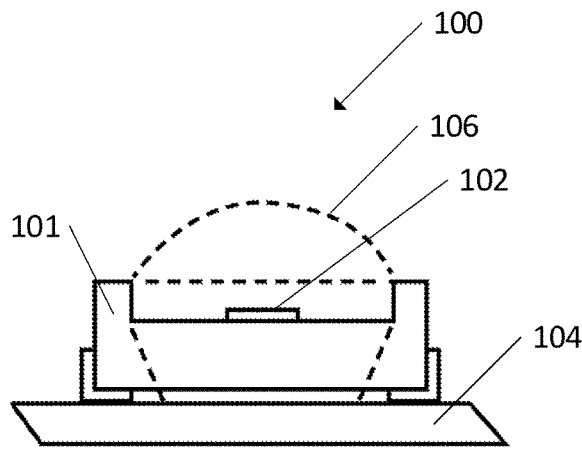
FIG. 1A                FIG. 1B
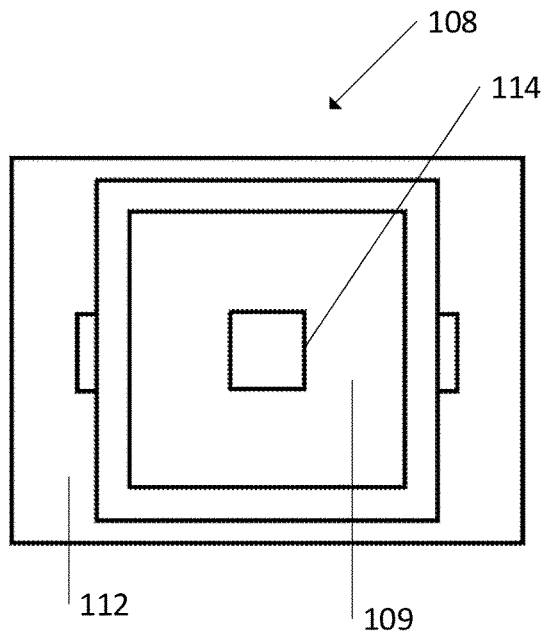
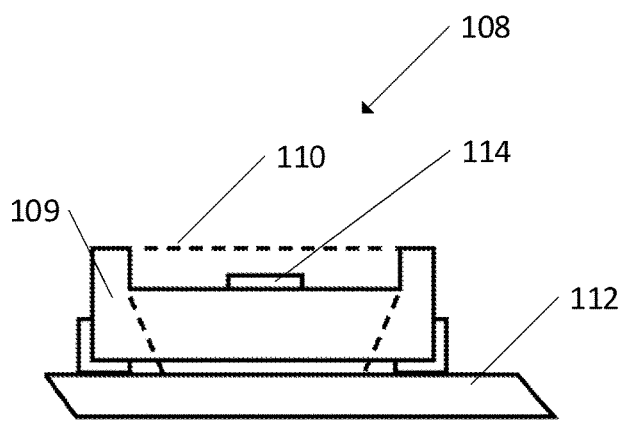
FIG. 1C                FIG. 1D

DISINFECTING LIGHT EMITTING SUBCOMPONENT

TECHNICAL FIELD

Aspects of the present disclosure generally relate to processes, systems, and apparatus for disinfecting light emitting subcomponents.

BACKGROUND

Many surfaces may be inhabited by harmful microorganisms: bacteria, mold, fungi, etc. due to the nature of their function. For example, a cleaning device (e.g., a mop) may comprise bacteria on its cleaning surfaces. As another example, surfaces such as a countertop used for food preparation may comprise bacteria due to human interaction. Microorganisms may transfer through contact with a surface, e.g., touching a door handle, and may cause illness to the users. Surfaces inhabited by harmful microorganisms may be external, e.g., countertops, or internal to a device, e.g., inside a humidifier. Harmful bacteria such as *Escherichia coli* (*E. coli*), *Salmonella*, Methicillin-resistant *Staphylococcus Aureus* (MRSA), and *Clostridium Difficile* may be found on many surfaces, and may increase the chance of a user becoming sick or transmitting the bacteria. For example, many surfaces within a kitchen, e.g., cutting boards, may come into contact with raw meat and vegetables which may contain bacteria that may lead to food-borne illnesses. Microorganisms located on internal or external surfaces may create unpleasant odors, e.g., bacteria on a wet mop, or create unpleasant visible effects, e.g., mold on shower surfaces. Harmful microorganisms may also be harbored on surfaces in commercial settings, such as, for example, food production lines, indoor agriculture grow rooms, and healthcare settings.

SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

In some examples, a light emitting device may comprise a substrate and one or more light emitters disposed on the substrate. The light emitters may be configured to inactivate microorganisms on a surface a distance away from the substrate by emitting a light. The light may comprise a proportion of a spectral energy of the light, measured in a 380 nanometers (nm) to 420 nm wavelength range, greater than 50%. The light may comprise a full width half max (FWHM) emission spectrum of less than 20 nm and centered at a wavelength of approximately 405 nm to concentrate the spectral energy of the light and minimize energy associated with wavelengths that bleed into an ultraviolet wavelength range. The light may comprise an irradiance at the surface sufficient to initiate inactivation of microorganisms on the surface.

In some examples, a method may comprise emitting, via one or more light emitters disposed on a substrate and to inactivate microorganisms on a surface a distance away from the substrate, a light. The light may comprise a proportion of a spectral energy of the light, measured in a 380 nm to 420 nm wavelength range, greater than 50%. The light may comprise a FWHM emission spectrum of less than 20 nm and centered at a wavelength of approximately 405 nm to concentrate the spectral energy of the light and minimize energy associated with wavelengths that bleed into an ultraviolet wavelength range. The light may comprise an irradiance at the surface sufficient to initiate inactivation of microorganisms on the surface. The light may cause, based on emission of the light, inactivation of the microorganisms on the surface.

In some examples, a light emitting device may comprise a substrate and an array of light emitting subcomponents disposed on the substrate. The light emitting subcomponents may be configured to inactivate microorganisms on a surface a distance away from the substrate by emitting a light. The light may comprise a proportion of a spectral energy of the light, measured in a 380 nanometers (nm) to 420 nm wavelength range, greater than 50%. The light may comprise a FWHM emission spectrum of less than 20 nm and centered at a wavelength of approximately 405 nm to concentrate the spectral energy of the light and minimize energy associated with wavelengths that bleed into an ultraviolet wavelength range. The light may comprise an irradiance at the surface sufficient to initiate inactivation of microorganisms on the surface. The light emitting device may comprise a controller disposed on the substrate and configured to adjust output of the array of light emitting subcomponents.

BRIEF DESCRIPTION OF THE DRAWINGS

Examples herein will be described in detail, with reference to the following figures, wherein like designations denote like elements.

FIGS. 1A-1B illustrate different views of an example light emitter on a substrate.

FIGS. 1C-1D illustrate different views of another example light emitter on a substrate.

DETAILED DESCRIPTION

Figure 2A:
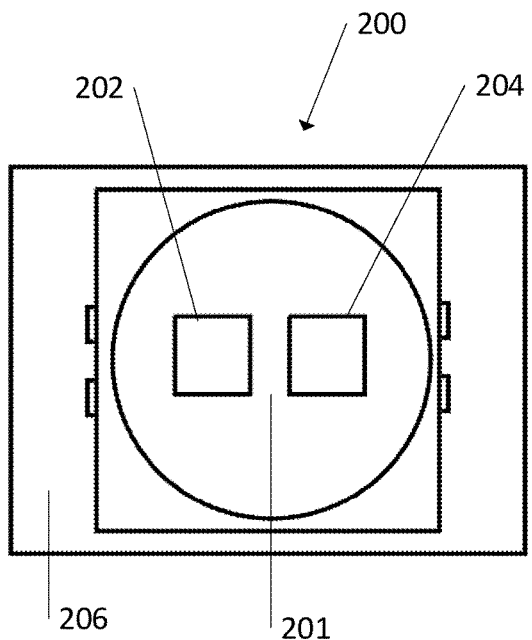
FIGS. 2A-2B illustrate different views of an example light emitter, on a substrate, with two lighting elements.

In the following description of the various examples, reference is made to the accompanying drawings, which form a part hereof, and in which is shown by way of illustration, various examples of the disclosure that may be practiced. It is to be understood that other examples may be utilized.

Surfaces may be disinfected in a number of ways. One technique may be cleaning with disinfecting chemical cleaners or soaps. Chemical cleaners may only provide intermittent disinfection, which may allow harmful microorganisms to build up between cleanings. Some disinfecting systems transmit ultraviolet (UV) light onto surfaces for disinfection. UV light exposure may be harmful for humans and animals, so UV light should be off when there may be a chance of user exposure. Accordingly, these systems may involve complex controls to prevent harmful, direct exposure to humans. Additionally, UV light may cause degradation and yellowing of material (e.g., plastic) and/or surfaces.

Wavelengths of visible light in the violet range, 380-420 nanometer (nm) (e.g., 405 nm), may have a lethal effect on microorganisms such as bacteria, yeast, mold, and fungi. For example, *Escherichia coli* (*E. coli*), *Salmonella*, Methicillin-resistant *Staphylococcus Aureus* (MRSA), and *Clostridium Difficile* may be susceptible to 380-420 nm light. These wavelengths may initiate a photoreaction with porphyrin molecules found in such microorganisms. The porphyrin molecules may be photoactivated and may react with other cellular components to produce Reactive Oxygen Species (ROS). ROS may cause irreparable cell damage and eventually destroy, kill, or otherwise inactivate cells of microorganisms. Because humans, plants, and/or animals do not contain the same porphyrin molecules, this technique may be completely safe for human exposure.

In some examples, inactivation, in relation to microorganism death, may include control of and/or reduction in microorganism colonies or individual cells when exposed to disinfecting light for a certain duration.

In some examples, light emitting subcomponents may be configured to disinfect by providing continuous and/or longer-term intermittent disinfection through the use of safe visible light. In some examples, longer-term intermittent disinfection may comprise continuous disinfection with minimal interruptions, e.g., disinfection for days or weeks without interruption. In some examples, longer-term intermittent disinfection may comprise continuous disinfection for at least 2 hours. In some examples, longer-term intermittent disinfection may comprise continuous disinfection for approximately 8 hours, e.g., overnight. The example light emitting subcomponents disclosed herein may be configured to be integrated into a larger assembly, e.g., a fixture or device.

Examples disclosed herein may include a subcomponent comprising at least one light emitter, wherein the at least one light emitter may be configured to emit light having a wavelength in the range of 380-420 nm. Light emitters may comprise any device capable of emitting light, such as, for example, semiconductor die, LEDs, LEDs with light-converting layer(s), laser, electroluminescent wires, electroluminescent sheets, flexible LEDs, or OLEDs. Light emitters, as described herein, may comprise any now known or later developed material appropriate for the stated wavelength such as, for example, indium gallium nitride (InGaN) or gallium nitride (GaN).

As disclosed herein, light with a peak wavelength of light, or in some examples, multiple peak wavelengths, in a range of approximately 380 nm 420 nm may be utilized for the inactivation of bacterial pathogens. For example, approximately 405 nm light may be used as the peak wavelength. In some examples, any wavelength within 380 nm to 420 nm may be utilized, and that the peak wavelength may include a specific wavelength plus or minus approximately 5 nm.

Radiant flux, measured in Watts, is the total power from a light source. Irradiance is the power per unit area at a distance away from the light source. In some examples, the target irradiance on a target surface from the light source may be 10 mW/cm². A 10 mW/cm² target irradiance may be provided, for example, by a light source with a radiant flux of 10 mW located 1 cm from the target surface. In another example, a light source may be located 5 cm from the target surface. With a target irradiance of 10 mW/cm², the light source may be configured to produce a radiant flux approximately 250 mW. These calculations may be approximately based on the inverse square law, as shown in Equation 1, where the excitation light source may be assumed to be a point source, E is the irradiance, I is the radiant flux, and r is the distance from the excitation light source to a target surface.

$$E \cong \frac{I}{r^2}$$ Equation 1

A minimum irradiance of light (e.g., in the 380-420 nm wavelength) on a surface may cause microbial inactivation. For example, a minimum irradiance of 0.02 milliwatts per square centimeter (mW/cm²) may cause microbial inactivation on a surface over time, e.g., several weeks. In some examples, an irradiance of 0.05 mW/cm² may inactivate microorganisms on a surface, but higher values such as 0.1 mW/cm², 0.5 mW/cm², 1 mW/cm², or 2 mW/cm² may be used for quicker microorganism inactivation. In some examples, even higher irradiances may be used over shorter periods of time, e.g., 3 to 10 mW/cm². In some examples where the light emitted is very close to the surface intended to be disinfected, e.g., 0.5 mm to 50 mm, even higher irradiances may be achieved, e.g., 10 to 50 mW/cm². Example light emitters disclosed herein may be configured to produce light with such irradiances at a given surface.

In some examples, light for microbial inactivation may include radiometric power sufficient to inactive at least one bacterial population, or in some examples, a plurality of bacterial populations. One or more light emitters may have some minimum amount of radiometric power (e.g., 10 mW, 20 mW, 100 mW, 1000 mW, or 3000 mW for one light emitter) measured from 380-420 nm light.

Dosage (measured in Joules/cm²) may be another metric for determining an appropriate irradiance for microbial inactivation over a period of time. Table 1 below shows example correlations between irradiance in mW/cm² and Joules/cm² based on different exposure times. These values are examples and many others may be possible.

TABLE 1

| Irradiance (mW/cm²) | Exposure Time (hours) | Dosage (Joules/cm²) |
| --- | --- | --- |
| 0.02 | 1 | 0.072 |
| 0.02 | 24 | 1.728 |
| 0.02 | 250 | 18 |
| 0.02 | 500 | 36 |
| 0.02 | 1000 | 72 |
| 0.05 | 1 | 0.18 |
| 0.05 | 24 | 4.32 |
| 0.05 | 250 | 45 |
| 0.05 | 500 | 90 |
| 0.05 | 1000 | 180 |
| 0.1 | 1 | 0.36 |
| 0.1 | 24 | 8.64 |
| 0.1 | 250 | 90 |
| 0.1 | 500 | 180 |
| 0.1 | 1000 | 360 |
| 0.5 | 1 | 1.8 |
| 0.5 | 24 | 43.2 |
| 0.5 | 250 | 450 |
| 0.5 | 500 | 900 |
| 0.5 | 1000 | 1800 |

TABLE 1-continued

| Irradiance (mW/cm$^2$) | Exposure Time (hours) | Dosage (Joules/cm$^2$) |
|---|---|---|
| 1 | 1 | 3.6 |
| 1 | 24 | 86.4 |
| 1 | 250 | 900 |
| 1 | 500 | 1800 |
| 1 | 1000 | 3600 |

Table 2 shows examples of dosages for inactivating example bacterial species using 405 nm light. Example dosages and other calculations shown herein may be examples from laboratory settings, and may not represent example dosages or calculations in other situations. For example, real world applications may require dosages or other calculations performed herein that may differ from example laboratory data. Inactivation may be measured by $Log_{10}$ reduction. Other dosages of 405 nm light may be used with other bacteria not listed below.

TABLE 2

| Organism | Recommended Dose (J/cm$^2$) for 1-Log Reduction in Bacteria |
|---|---|
| Staphylococcus aureus | 20 |
| MRSA | 20 |
| Pseudomonas aeruginosa | 45 |
| Escherichia coli | 80 |
| Enterococcus faecalis | 90 |

Equation 2 may be used in order to determine irradiance, dosage, or time using one or more data points from Table 1 and Table 2:

$$\frac{\text{Irradiance}\left(\frac{mW}{cm^2}\right)}{1000} * \text{Time(s)} = \text{Dosage}\left(\frac{J}{cm^2}\right) \quad \text{Equation 2}$$

Irradiance may be determined based on dosage and time. For example, if a dosage of 30 Joules/cm$^2$ is desired and the object to be disinfected is going to be exposed to light overnight for 8 hours, the irradiance may be approximately 1 mW/cm$^2$. If a dosage of 50 Joules/cm$^2$ is desired and the object to be disinfected is going to be exposed to light for 48 hours, a smaller irradiance of approximately 0.3 mW/cm$^2$ may be sufficient.

A period of time to power the example light emitting subcomponents disclosed herein may be determined based on irradiance and dosage. For example, a device may be configured to emit an irradiance of disinfecting energy (e.g., 0.05 mW/cm$^2$), and a target bacterium may require a dosage of 20 Joules/cm$^2$ to kill the target bacteria. Disinfecting light at 0.05 mW/cm$^2$ may have a minimum exposure time of approximately 4.6 days to achieve the dosage of 20 Joules/cm$^2$. Dosage values may be determined by a target reduction in bacteria. Once the bacteria count is reduced to a desired amount, disinfecting light may be continuously applied to keep the bacteria counts down.

Various colors of light may be utilized with a percentage (e.g., 75%) of their spectral power distribution within the wavelength range of 380-420 nm. In some examples, colors of light may be utilized with a percentage of 30% to 100% spectral power distribution within the wavelength range of 380-420 nm. In other examples, colors such as, for example, blue, green, and red, may be used with a minimum percentage of spectral energy (e.g., 20%) within the range of 380-420 nm, which may provide disinfecting energy.

A proportion of spectral energy may be determined by an amount of spectral energy within a specified wavelength range, e.g., 380-420 nm, divided by the total amount of spectral energy. Proportions of spectral energy may be presented as a percentage of the total amount of energy In some examples, light provided in the wavelength range of 380-420 nm may not be adequate for general illumination purposes due to the violet color and low color quality characteristics. In some examples, this light may be used in spaces unoccupied by humans or spaces where additional white lighting for general illumination is already used. In some examples where a light emitting subcomponent is integrated into a device, e.g., humidifier, general white light illumination may not be required.

In some examples, continuous disinfection may be employed. For example, a surface intended to be disinfected may be continuously illuminated (e.g., illuminated 19 hours per day or multiple weeks at a time). A surface may be illuminated for a first percentage of time (e.g., 80% of the time) and not illuminated for a second percentage of time (e.g., 20% of the time). For example, a surface or object may not be illuminated when the object or surface is being interacted with, e.g., when using a cutting board. In some examples, intermittent disinfection may be employed, such as, for example, a surface may only be illuminated and disinfected at night, e.g., 8 hours per day.

In examples disclosed herein, a light emitting subcomponent 100 may comprise a light emitter 101 as shown in FIGS. 1A-1B. The light emitter 101 may comprise a lighting element 102, e.g., an LED die. The light emitting subcomponent 100 may further comprise a substrate 104 and a circular light directing material 106, e.g., a lens. The light directing material 106 may cover the lighting element 102, such that light provided by the lighting element 102 may pass through the light directing material 106. In some examples, the light directing material 106 may be in a direct path of light emitted from the lighting element 102 without entirely covering the lighting element 102. In some examples, the light directing material 106 may comprise a domed shape over the lighting element 102 as shown in FIG. 1B.

In some examples, the lighting element 102 may comprise any device capable of emitting light, such as, for example, semiconductor die, LEDs, LEDs with light-converting layer(s), laser, electroluminescent wires, electroluminescent sheets, flexible LEDs, and OLEDs.

FIGS. 1C-1D illustrate a light emitting subcomponent 108 with a rectangular light directing material 110. The light emitting subcomponent 108 may comprise light emitter 109 and a substrate 112. The light emitter 109 may comprise a lighting element 114. The light directing material 110 may cover the lighting element 114, such that light provided by the lighting element 114 may pass through the light directing material 110. In some examples, the light directing material 110 may be in a direct path of light emitted from the lighting element 114 without entirely covering the lighting element 114. The light directing material 110 may comprise a flat orientation perpendicular to light emitted by the lighting element 114 as is shown in FIG. 1D.

Figure 2B:
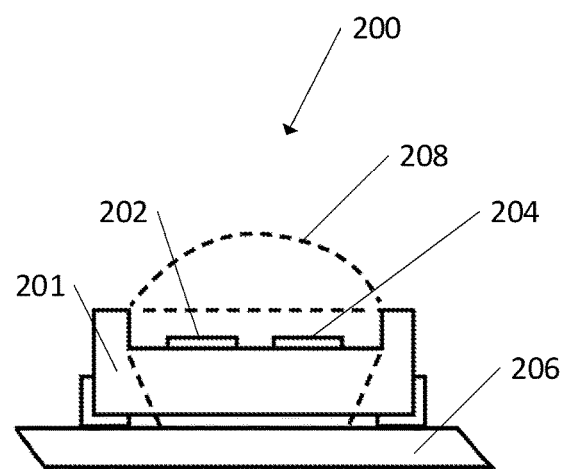

FIGS. 2A-2B show a light emitting subcomponent 200 that may comprise a light emitter 201. The light emitter 201 may comprise a first lighting element 202 and a second lighting element 204. In some examples, the first lighting element 202 and the second lighting element 204 may be the same and emit substantially similar light. In other examples, the first lighting element 202 and the second lighting element 204 may be different, e.g., emit light of different spectral power distributions. The light emitting subcomponent 200 may comprise a substrate 206. The light emitter 201 may comprise a circular light directing material 208. The light directing material 208 may cover the first lighting element 202 and the second lighting element 204 such that light provided by first lighting element 202 and the second lighting element 204 may pass through the light directing material 208. In some examples, the light directing material 208 may be in a direct path of light emitted from the first lighting element 202 and the second lighting element 204 without entirely covering the first lighting element 202 and the second lighting element 204. In some examples, the light directing material 208 may be in a direct path of light emitted from or entirely cover only one of the first lighting element 202 or the second lighting element 204. In some examples, the light directing material 208 may comprise a domed shape over the first lighting element 202 and the second lighting element 204 as shown in FIG. 2B.

Figure 2C:
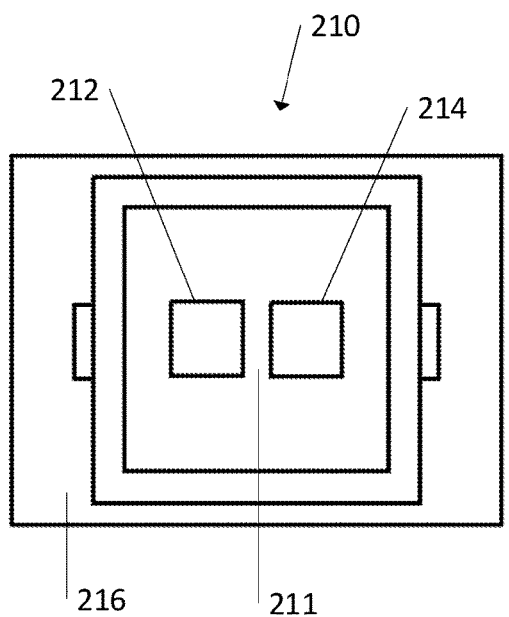
FIGS. 2C-2D illustrate different views of another example light emitter, on a substrate, with two lighting elements.
Figure 2D:
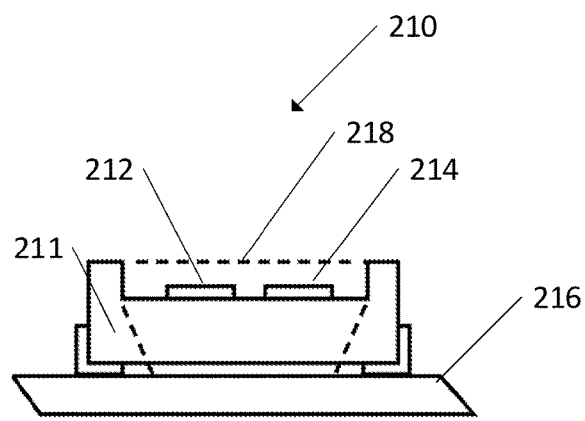

FIGS. 2C-2D show a light emitting subcomponent 210 that may comprise a light emitter 211. The light emitter 211 may comprise a first lighting element 212 and a second lighting element 214. In some examples, the first lighting element 212 and the second lighting element 214 may be the same and emit substantially similar light. In other examples, the first lighting element 212 and the second lighting element 214 may be different, e.g., emit light of different spectral power distributions. The light emitting subcomponent 210 may comprise a substrate 216 and a square light directing material 218. The light directing material 218 may cover the first lighting element 212 and the second lighting element 214 such that light provided by first lighting element 212 and the second lighting element 214 may pass through the light directing material 218. In some examples, the light directing material 218 may be in a direct path of light emitted from the first lighting element 212 and the second lighting element 214 without entirely covering first lighting element 212 and the second lighting element 214. In some examples, the light directing material 218 may be in a direct path of light emitted from or entirely cover only one of the first lighting element 212 or the second lighting element 214. In some examples, the light directing material 218 may comprise a domed shape over the first lighting element 212 and the second lighting element 214 as shown in FIG. 2D.

Figure 3A:
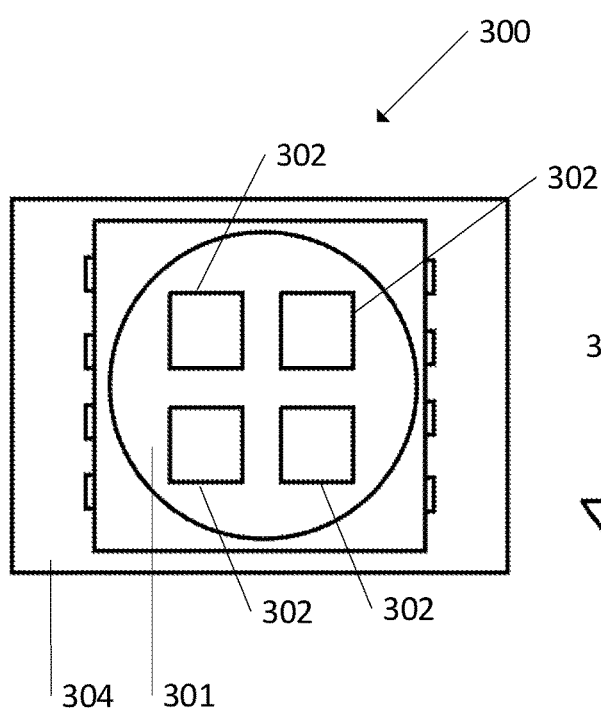
FIGS. 3A-3B illustrate different views of an example light emitter, on a substrate, with four lighting elements.
Figure 3B:
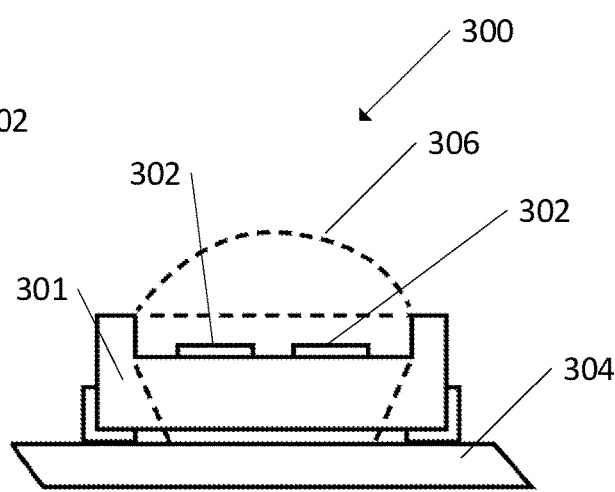

FIGS. 3A-3B show a light emitting subcomponent 300 that may comprise a light emitter 301. The light emitter 301 may comprise four lighting elements 302. In some examples, each of the four lighting elements 302 may be the same and emit substantially similar light. In other examples, the four lighting elements 302 may be different, e.g., emit light of different spectral power distributions. In other examples, any other combination of similar or dissimilar lighting elements 302 may be used. The light emitting subcomponent 300 may comprise a substrate 304 and a circular light directing material 306. The light directing material 306 may cover the lighting elements 302, such that light provided by the lighting elements 302 may pass through the light directing material 306. In some examples, the light directing material 306 may be in a direct path of light emitted from the lighting elements 302 without entirely covering the lighting elements 302. In some examples, the light directing material 306 may be in a direct path of light emitted from or entirely cover only number of the lighting elements 302. In some examples, the light directing material 306 may comprise a domed shape over the lighting elements 302 as shown in FIG. 3B.

In some examples, the light directing material 306 may comprise light-converting materials such as, for example, filters, diffusers, and/or optics that may be used to provide optical filtering (e.g., high pass, bandpass, or low pass filter functionality). For example, if light within the range of 400-420 nm is desired, an optical filtering element may cut off wavelengths above, below, and/or outside a desired range. Optical filtering may reduce or block any potentially harmful wavelengths, e.g., below 380 nm. Optical filtering may reduce the risk of UV exposure or material degradation due to UV wavelengths. In some examples, a light-converting material, filter, diffuser, and/or optical filtering elements that may be used to provide optical filtering may be external to the light emitting subcomponent 300, and in some examples, may cover the light emitter 301 or the entire light emitting subcomponent 300.

Material choice for lenses, diffusers, reflectors, optics, protective shields, and other transmissive components of a light fixture or light bulb may contribute to the overall efficiency of the light emitting subcomponents 100, 108, 200, 210, 300. The choice of material(s) may affect transmission and/or reflection efficiencies. Reflectors and/or transmissible components for general illumination sources (e.g., incandescent bulbs, fluorescent bulbs, and RGB/blue pump phosphor converted LEDS) may include, for example, plastics, glasses, coatings, and other materials. Incandescent bulbs, fluorescent bulbs, and RGB/blue pump phosphor converted LEDS may rely very little on near-UV wavelengths to provide illumination. Additionally, many of these reflectors or transmissive components may exhibit a sharp drop off in reflectance or transmission efficiency (e.g., close to zero in some examples) for wavelengths of light in the near-UV range, e.g., the wavelength is approximately 380 to 420 nm. Light fixtures or light bulbs made of improper reflective or transmissive materials may cause light in the 380-420 nm range to show a decrease in spectral energy. Reflective and transmissive materials may be selected based on the output of light from a light source. In some examples, a diffuser may allow at least 50% total transmission in the 380-420 nm range. In some examples, a diffuser may allow at least 75% total transmission in the 380-420 nm range.

In some examples, the material for a reflector or diffuser may be selected such that it may transmit as much 380-420 nm light as possible. In some examples, it may be desirable to select materials (e.g., plastics, resins, thermoplastic resins, or polymers) that may not substantially absorb light in the 380-420 nm range.

In some examples, the lighting element 102, 114, 202, 204, 212, 214, 302 may have a small full width at half maximum (FWHM) emission spectrum (e.g., 12.5 nm, 13.5 nm, 14.7 nm, 16 nm, 20 nm) in order to concentrate energy surrounding a peak of approximately 405 nm. Concentrating energy to a target range where it provides disinfection minimizes waste of non-useful energy outside of the target range. Concentrating energy to a FWHM emission spectrum may increase safety by reducing the intensity of wavelengths that may bleed into the UV range. In some examples, the FWHM may be less than 20 nm, between 12 and 20 nm, and/or 13.5 nm. In some examples, the light directing material 106, 110, 208, 218, 306 may provide the desired small FWHM emission spectrum. In some examples, the light directing material 106, 110, 208, 218, 306 may provide the desired small FWHM emission spectrum by, for example, providing filtering or light conversion.

In some examples, the light directing material 106, 110, 208, 218, 306 may comprise a phosphor, an optical brightener, a combination of phosphors, a combination of optical brighteners, or a combination of phosphor(s) and optical brightener(s). In some examples, the light directing material 106, 110, 208, 218, 306 may comprise quantum dots, a phosphorescent material, a fluorophore, a fluorescent dye, a conductive polymer, or a combination of any one or more types of light-converting materials. In some examples, the light directing material 106, 110, 208, 218, 306 may comprise an activator (e.g., a light-converting element) and a host (e.g., a non-light-converting element). A phosphor or other light-converting material may be deposited directly on a light emitting subcomponent, as disclosed herein, or may be remote or further removed from the lighting element 102, 114, 202, 204, 212, 214, 302. Light-converting materials may be deposited, for example, as conformal coatings, doped encapsulants, binder materials, or remote phosphors.

In some examples, it may be desirable to dissipate heat generated by lighting elements or other components of a light emitter as disclosed herein. A decreased operating temperature may increase reliability and lifetime of a device. Heat may affect the peak wavelength and spectrum emitted by the LEDs. For example, as temperatures rise, peak wavelengths may shift to longer wavelengths and/or the entire spectrum may be moved away from UV light and towards visible light. Similarly, as temperatures decrease, peak wavelengths may shift to shorter wavelengths and/or and the entire spectrum may be moved away from visible light and towards UV light. Therefore, it may be desirable to constrain the temperature to a certain range in order to maintain a desired peak wavelength or spectrum within some tolerance. In some examples, the light emitter may be coupled to a heatsink (not shown). The heatsink may be made out of plastics, ceramics, or metals including, for example, aluminum, steel, or copper. The heatsink may also be made out of a plastic or ceramic material. In some examples the heatsink may be permanently coupled to a light emitter, or otherwise considered a part of the assembly that makes up the light emitter or light emitting subcomponent.

Figure 4A:
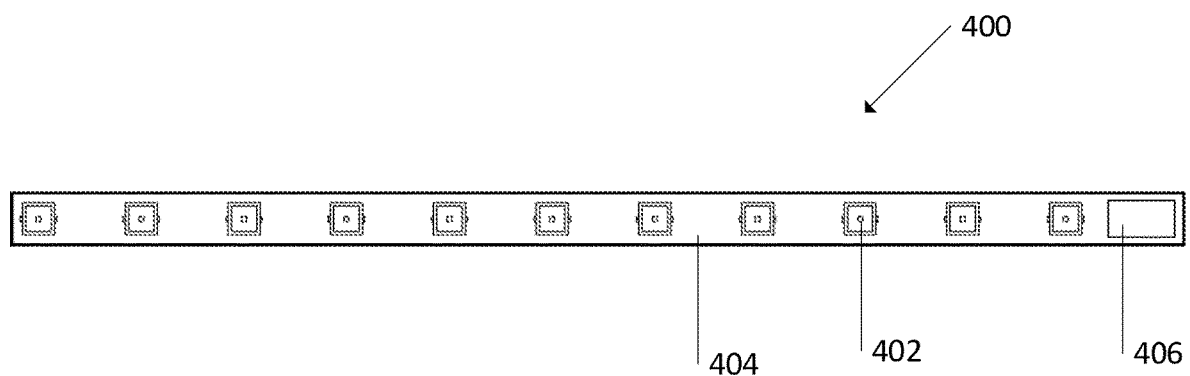
FIGS. 4A-4B illustrate example strip light emitting subcomponent.
Figure 4B:
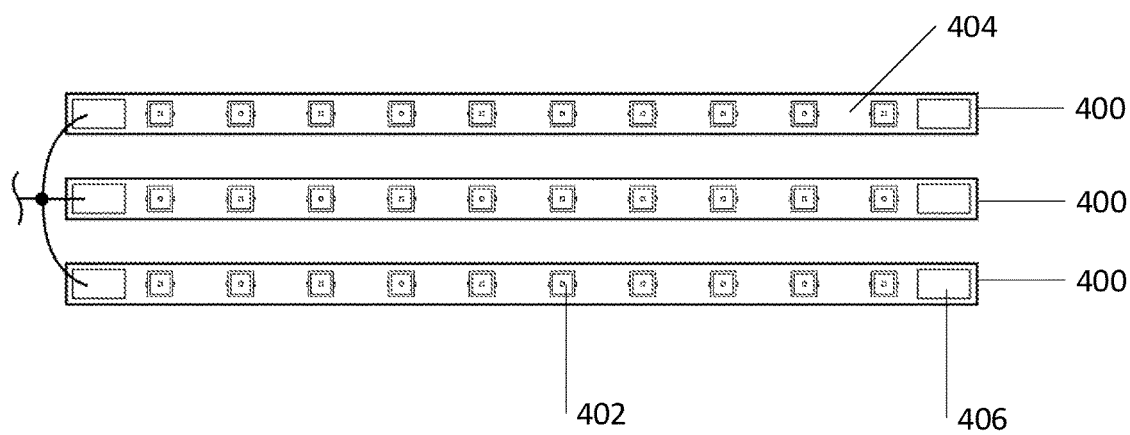

In some examples, a substrate 104, 112, 206, 216, 304, 404 of a light emitting subcomponent 400 with light emitters 101, 109, 201, 211, 301 may comprise a circuit board or printed circuit board as shown in FIG. 4A. In some examples, the circuit board of the light emitting subcomponent 400 may be populated with light emitters 402. In some examples, the circuit board may contain or be connected to control circuitry 406 that may control the light emitted from the light emitters 402. In some examples, the control circuitry 406 may determine the number of light emitters 402 to be powered. The control circuitry 406 may control the light emitters 402 and determine which light emitters 402 to turn on based on a number of factors such as, for example, distance between the light emitting subcomponent 400 and a surface to be disinfected, time, a threshold irradiance necessary to initiate inactivation of a microorganism to be inactivated, and the irradiance provided by a single light emitter 402. The control circuitry 406 may also control, for example, the amount of time the light emitters 402 are on or off, and may comprise occupancy sensors, e.g., motion sensors. The control circuitry 406 may be configured to adjust the light emitting subcomponent 400 based on the occupancy sensors, e.g., adjusts the concentration of spectral energy at specific wavelengths.

The light emitters 402 and control circuitry 406 may be configured to connect to a power source (not shown). In some examples, the light emitters 402, light emitting subcomponents 400, light fixtures, or devices disclosed herein may be powered through power outlets, electrical power supplies, batteries or rechargeable batteries, and/or wireless or inductive charging. In some examples that comprise rechargeable batteries, the rechargeable batteries may be recharged by, for example, AC power or solar panels. In some examples, AC power and an AC to DC converter, e.g., an LED driver or power supply, may be utilized. In some examples, direct DC power may be utilized when available. In some examples, wireless or inductive charging may charge or power the light fixture or device.

The substrate 404 of a light emitting subcomponent 400 may vary in material, shape, size, thickness, flexibility, and otherwise be conformed to specific applications. Base material of the substrate 404 may comprise a variety of materials such as, for example, aluminum, FR-4 (glass-reinforced epoxy laminate material), Teflon, polyimide, or copper.

FIGS. 4A-6 show a number of different light emitting subcomponent shapes, such as, for example, straight, circular, or rectangular. An array of light emitting subcomponents may be formed from multiple light emitting subcomponents 400. In some example, an array of light emitting subcomponents may comprise multiple connected light emitting subcomponents 400 as shown in FIG. 4B. The control circuitry 406 may vary the shape of the array that is providing illumination based on determining which light emitters 402 to power, e.g., the control circuitry 406 may power a portion of the light emitters 402 to illuminate a smaller area than may be covered by illuminating the entire array of light emitting subcomponents 400.

Figure 5A:
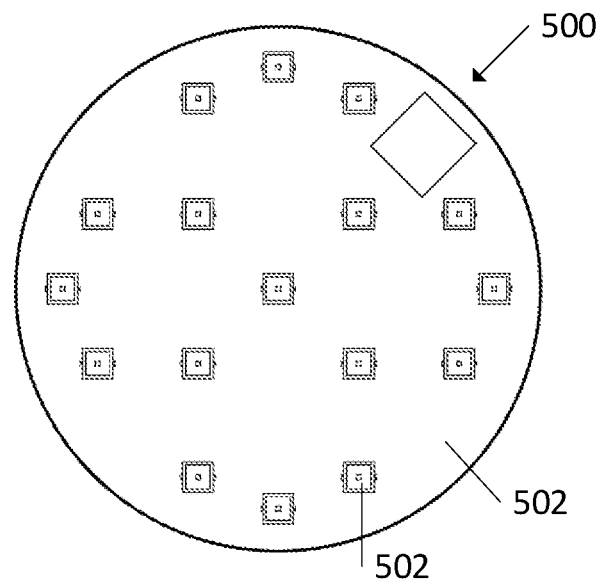
FIGS. 5A-5B illustrate example circular light emitting subcomponent.
Figure 5B:
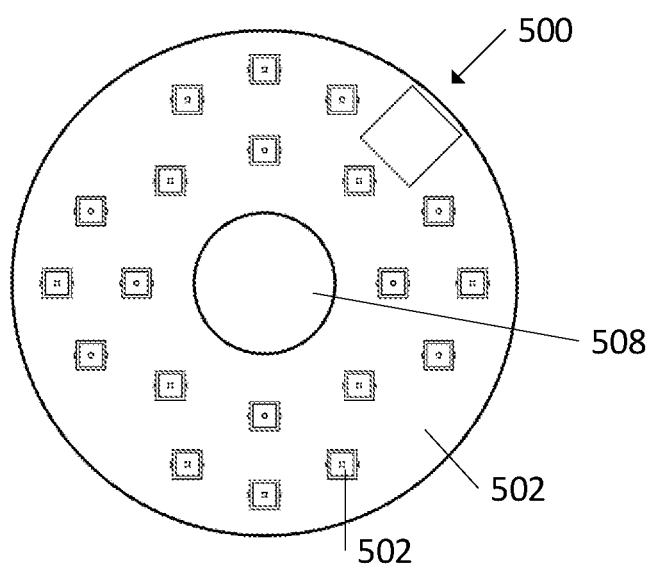

In some examples, a light emitting subcomponent 500 may form a circle as shown in FIGS. 5A-5B. FIG. 5A shows a light emitting subcomponent 500 with a circular substrate 504 and light emitters 502 arranged circularly thereon. FIG. 5B shows a similar light emitting subcomponent 500 where the circular substrate 504 has a hole 506 within it.

Figure 6:
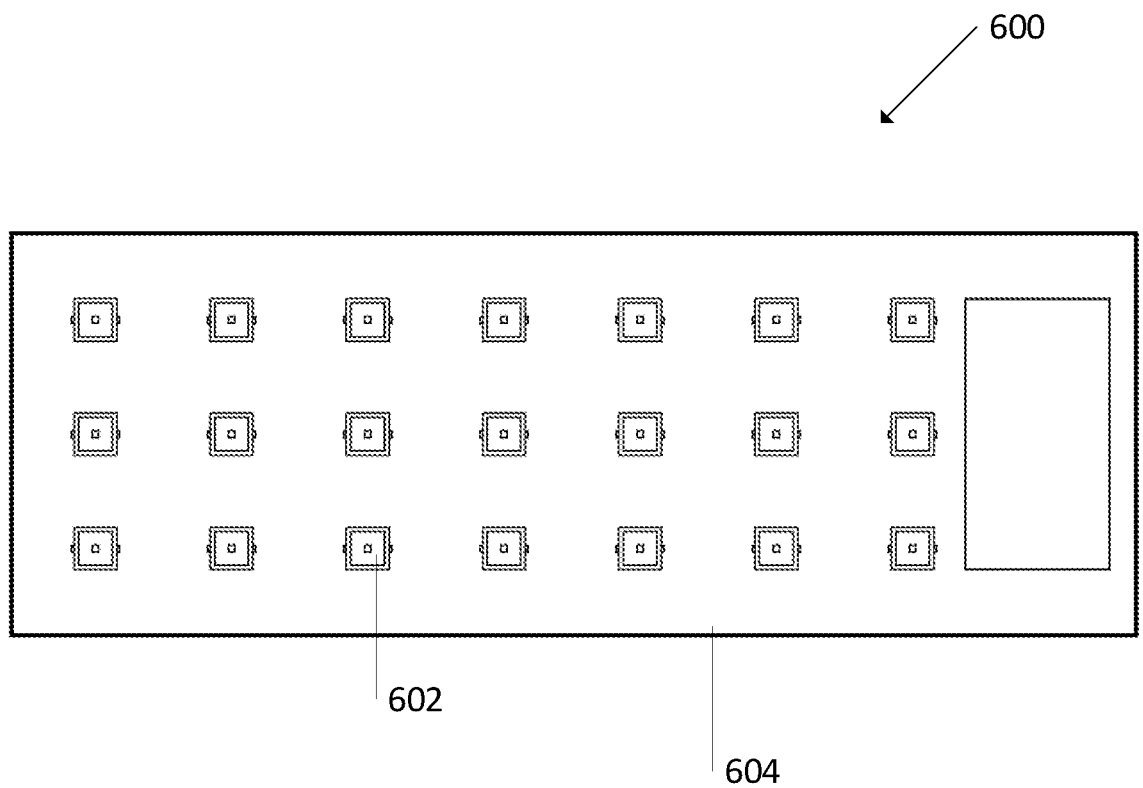
FIG. 6 illustrates an example rectangular light emitting subcomponent.

In some examples, a light emitting subcomponent 600 may form a rectangle as shown in FIG. 6. FIG. 6 shows a light emitting subcomponent 600 with a rectangular substrate 604 and light emitters 602 arranged thereon.

In some examples, a light emitter or a light emitting subcomponent may comprise a conformal coating. The conformal coating may comprise a polymeric film contoured to the light emitting subcomponent. The conformal coatings may provide ingress protection from, for example, condensation or other liquids.

Figure 7A:
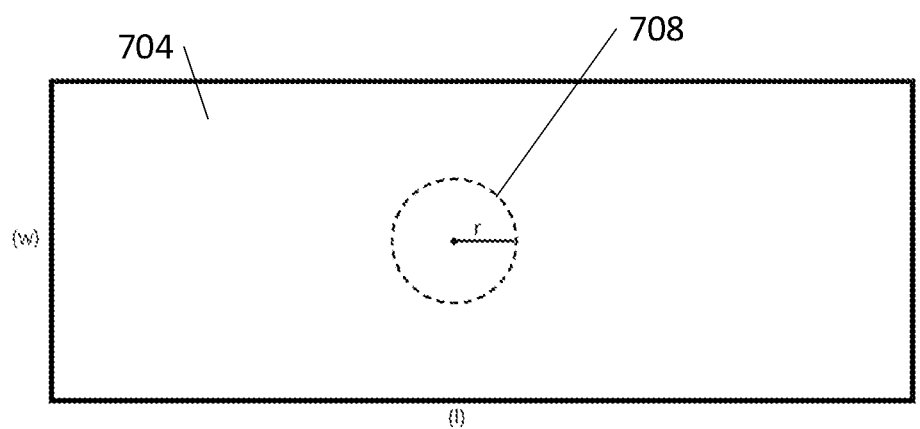
FIGS. 7A-7B illustrate an example relationship between LED beam angles and a corresponding illuminated surface to cause inactivation.

In some examples, a surface to be disinfected may be in close proximity to a light emitting subcomponent. In such examples, a light emitting subcomponent or an array of light emitting subcomponents may require more light emitters than would otherwise be necessary for disinfection. The area illuminated by a single light emitter may be limited by a beam angle of the light emitter. The same light emitter may illuminate a larger surface area of the surface to be disinfected if the light emitter is moved further away. Therefore, a light emitting subcomponent may need an increased number of light emitters to cover the entire surface area of the surface to be disinfected with disinfecting light, as compared to a light emitting subcomponents at a further distance. FIG. 7A illustrates angles of light emitted from light emitters disclosed herein. Light emitters 700 may be spaced a distance 702 from the surface 704 to be disinfected. The light emitters 700 may emit a light that spreads outwardly toward the surface 704 at a beam angle 706. The beam angle 706 may comprise half of an angle of light emitted from the light emitter 700, in degrees, where the intensity of light is at least 50% of light emitter's 700 maximum emission intensity. In some examples, the light emitter 700 may comprise LEDs and the beam angle 706 may be 130 degrees, e.g., the angle of light emitted from the light emitter where the intensity of light is at least 50% of the maximum emission intensity is 130 degrees. In some examples where light from the light emitter 700 does not possess rational symmetry, the beam angle 702 may be given for two planes at 90 degrees to each other.

Figure 7B:
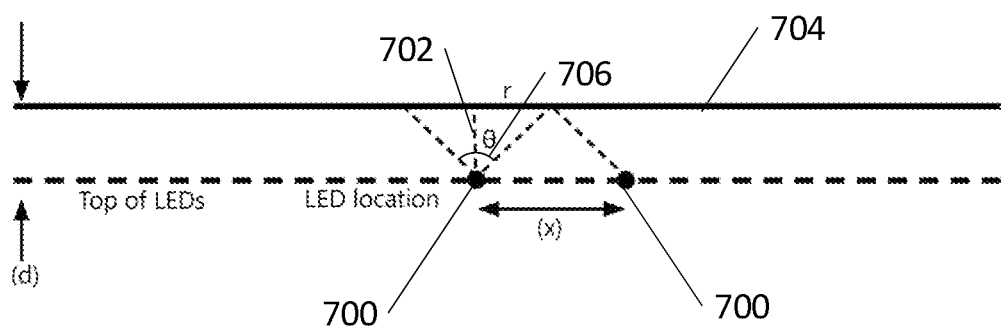

A total surface area illuminated by one light emitter 708, as shown in FIG. 7B, may be determined by the beam angle 706 and the distance 702 from the light emitter 700 to the surface 704 intended to be disinfected. A light emitter 700 with a larger beam angle 706 may provide a larger total surface area illuminated by one light emitter 708. An increased distance 702 between the light emitter 700 and the surface 704 may also increase the total surface area illuminated by one light emitter 708. The total number of light emitters 700 that may be needed to disinfect the entire surface 704 to be disinfected may be based on the total surface area illuminated by one light emitter 708. As the distance 702 from the surface 704 intended to be disinfected to the light emitter 700 decreases, the number of light emitters 700 that may be needed to disinfect the surface may increase.

In some examples, the surface 704 intended to be disinfected may be a protective layer over the light emitters 700. In other examples, the surface 704 to be disinfected may be an object that may be placed on top of a protective surface over the light emitters 700, e.g., a cell phone. In some examples, the total surface area illuminated by one light emitter 708 may be substantially the same as a surface area the surface 704 to be disinfected, such as, for example, when the light emitter 700 is close (e.g., 2 cm or less) to the surface 704 to be disinfected. In some examples the total surface area illuminated by one light emitter 708 may not be the same as the surface area the surface 704 to be disinfected.

In one example, the total surface area illuminated by a light emitting subcomponent may be 15 cm×15 cm and the surface area the surface 704 to be disinfected may be substantially the same size. If the distance 702 from the light emitting subcomponent to the surface 704 is 1.5 cm, and the light emitters 700 have a beam angle of 130 degrees, the total surface area illuminated by one light emitter 708 may be 32.5 cm$^2$, and the light emitting subcomponent may need 7 light emitters 700 to cover the entire surface 704. In another example, the total surface area illuminated by a light emitting subcomponent may be 100 cm×100 cm and the surface area the surface 704 to be disinfected may be substantially the same size. If the distance 702 from the light emitting subcomponent to the surface 704 is 1 cm, and the light emitters 700 have a beam angle of 130 degrees, the light emitting subcomponent may need 693 light emitters 700. In another example, the total surface area illuminated by a light emitting subcomponent may be 100 cm×100 cm and the surface area the surface 704 to be disinfected may be substantially the same size. If the distance 702 from the light emitting subcomponent to the surface 704 is 4 cm, and the light emitters 700 have a beam angle of 130 degrees, the total surface area illuminated by one light emitter 708 may be 231.2 cm$^2$, and light emitting subcomponent may need 44 light emitters 700.

Figure 8:
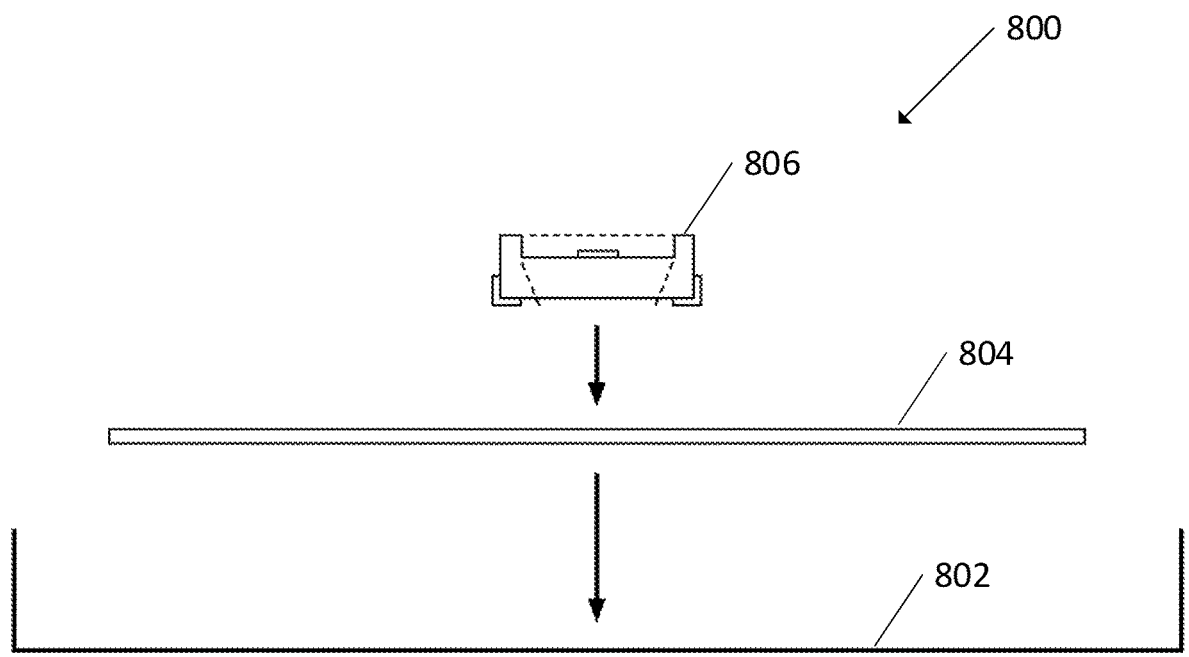
FIG. 8 illustrates an example light emitter and a corresponding substrate and housing.

In some examples, a light emitting subcomponent may be configured to be integrated into an assembly of a fixture or device. FIG. 8 shows a lighting device 800. The lighting device 800 may comprise a light housing 802. A light emitting subcomponent may be attached or otherwise mounted to or within the light housing 802. The light emitting subcomponent may comprise a substrate 804 with a light emitter 806 forming the light emitting subcomponent. The fixture or device that may comprise the light housing 802 may be, for example, a humidifier (not shown).

By way of example, various light emitters and light emitting subcomponents and features are discussed below. Such features may be separated, combined, rearranged, and/or used together. In some examples, a light emitter may comprise a surface mount LED device, which may include an LED and a light-conversion material. The surface mount LED device may, in some examples, be mounted onto a printed circuit board ("PCB") or otherwise configured to transfer power to the light-emitting device and to the LED. The LED may be coupled to the PCB through bond wires or leads which enable an electrical connection from the LED to the outside of the device. In some examples, the surface mount LED device may have a lens, encapsulants, or other protective cover.

In some examples, the light emitter may comprise a chip scale package (CSP) or a flip chip CSP, which may package the light emitters without using a traditional ceramic/plastic package and/or bond wires, and may enable a substrate to be attached directly to the PCB.

In some examples, there may be more than one light emitter and the light emitters may be arranged in an approximately evenly spaced array.

In some examples, a light emitting subcomponent may comprise an array of LEDs contained by a light-converting material that may be contained by an encapsulant and supported on a substrate.

In some examples, a light fixture or device may be integrated with one or more light emitting subcomponents. The light fixture or device may comprise additional materials and components, e.g., LED drivers, housings, plastic diffusers, endcaps, wiring harnesses, control circuitry, hardware, and/or means for mounting the light emitting subcomponent.

In some examples, the light emitting subcomponent may be a circuit board.

In some examples, the light emitting subcomponent may be made of aluminum.

In some examples, the light emitting subcomponent may be made of FR-4.

In some examples, the light emitting subcomponent may be populated with one or more light emitters.

In some examples, the one or more light emitters may be one or more light emitting diodes (LEDs).

In some examples, the one or more light emitters may emit light in a range of 380-420 nm.

In some examples, the one or more light emitters may emit a light with a peak wavelength of approximately 405 nm.

In some examples, the light emitted by the one or more light emitters may be substantially the same.

In some examples, the light emitted by the one or more light emitters may have a full width half max of no more than 20 nm.

In some examples, the light emitting subcomponent may be flexible.

In some examples, the light emitting subcomponent may be rigid.

In some examples, the one or more light emitters may be configured to provide an irradiance on a target surface of at least 0.1 mW/cm$^2$.

In some examples, the one or more light emitters may be configured to provide an irradiance on a target surface of between 0.1 and 10 mW/cm$^2$.

In some examples, the light emitting subcomponent may be configured to inactivate microorganisms on a surface.

In some examples, the light emitting subcomponent may comprise or otherwise be connected to driving circuitry that may control the light output.

In some examples, the size and flexibility of the light emitting subcomponent may be customized for various applications.

In some examples, the light emitting subcomponent may comprise an adhesive back.

In some examples, the light emitting subcomponent may comprise components other than light emitters.

In some examples, only one side of the light emitting subcomponent may be populated with light emitters and/or components.

In some examples, both sides of the light emitting subcomponent may be populated with light emitters and/or components.

In some examples, the light emitting subcomponent may be connected to an LED driver that controls the voltage and current provided the light emitting subcomponent.

In some examples, the control circuitry may be able to control the output of the light including the brightness and/or duration of illumination.

In some examples the light emitting subcomponent may be conformal coated for protection of the one or more light emitters.

In some examples, a light emitting device may comprise a substrate and one or more light emitters disposed on the substrate. The light emitters may be configured to inactivate microorganisms on a surface a distance away from the substrate by emitting a light. The light may comprise a proportion of a spectral energy of the light, measured in a 380 nanometers (nm) to 420 nm wavelength range, greater than 50%. The light may comprise a full width half max (FWHM) emission spectrum of less than 20 nm and centered at a wavelength of approximately 405 nm to concentrate the spectral energy of the light and minimize energy associated with wavelengths that bleed into an ultraviolet wavelength range. The light may comprise an irradiance at the surface sufficient to initiate inactivation of microorganisms on the surface.

In some examples, the irradiance at the surface sufficient to initiate inactivation of microorganisms on the surface may comprise at least 0.02 milliwatts per square centimeter (mW/cm$^2$).

In some examples, the light emitting device may comprise a sensor configured to detect occupancy of an area comprising the surface. The light emitting device may comprise a controller configured to adjust, based on the sensor detecting occupancy of the area, the proportion of the spectral energy, measured in the 380 nm to 420 nm wavelength range, of the light between 0% and 100%.

In some examples where the light is a first light, the light emitting device may comprise a conversion material arranged in a direct path of the first light and configured to generate, based on the first light, a second light comprising a wavelength outside the 380 nm to 420 nm wavelength range.

In some examples, the substrate of a light emitting device may comprise one or more of aluminum, glass-reinforced epoxy laminate, Teflon, polyimide, or copper.

In some examples, the light emitters may comprise one or more light emitting diodes (LEDs).

In some examples, one or more light emitters may be configured as an array of light emitters on the substrate.

In some examples, a number of the one or more light emitters may be determined based on the distance that the surface is away from the substrate, based on the size of the surface, based on a microorganism to be inactivated, or based on a beam angle of at least one of the one or more light emitters.

In some examples, one or more light emitters may be arranged based on the distance that the surface is away from the substrate, based on the size of the surface, based on a microorganism to be inactivated, or based on a beam angle of at least one of the one or more light emitters.

In some examples, a radiometric power of the light emitted by the one or more light emitters may be based on the distance that the surface is away from the substrate, based on the size of the surface, based on a microorganism to be inactivated, or based on a beam angle of at least one of the one or more light emitters.

In some examples, the FWHM emission spectrum of the light from the light emitting device may comprise an FWHM emission spectrum corresponding to light measured in the 380 nm to 420 nm wavelength range.

In some examples, a method may comprise emitting, via one or more light emitters disposed on a substrate and to inactivate microorganisms on a surface a distance away from the substrate, a light. The light may comprise a proportion of a spectral energy of the light, measured in a 380 nm to 420 nm wavelength range, greater than 50%. The light may comprise a FWHM emission spectrum of less than 20 nm and centered at a wavelength of approximately 405 nm to concentrate the spectral energy of the light and minimize energy associated with wavelengths that bleed into an ultraviolet wavelength range. The light may comprise an irradiance at the surface sufficient to initiate inactivation of microorganisms on the surface. The light may cause, based on emission of the light, inactivation of the microorganisms on the surface.

In some examples of the method, the irradiance at the surface sufficient to initiate inactivation of microorganisms on the surface may comprise at least 0.02 milliwatts per square centimeter (mW/cm$^2$).

In some examples, the method may comprise detecting, via a sensor, occupancy of an area comprising the surface. The method may comprise adjusting, via a controller in communication with the sensor and the one or more light emitters and based on the detecting occupancy of the area, the proportion of spectral energy, measured in the 380 nm to 420 nm wavelength range, of light between 0% and 100%.

Some examples of the method, where the light is a first light, may comprise causing conversion of the first light, via a conversion material arranged in a direct path of the first light, of the first light to a second light comprising a wavelength outside the 380 nm to 420 nm wavelength range.

In some examples, the method may comprise configuring the one or more light emitters as an array of light emitters on the substrate.

Some examples of the method may comprise determining the distance between the light emitters and the surface and determining a size of the surface. The method may further comprise determining, based on the determined distance between the light emitters and the surface, based on the size of the surface, based on a microorganism to be inactivated, or based on a beam angle of at least one of the one or more light emitters, a number of light emitters to inactivate the microorganism. The method may comprise powering the determined number of light emitters for a period of time.

In some examples, the one or more light emitters may be arranged based on the distance that the surface is away from the substrate, based on a size of the surface, based on a microorganism to be inactivated, or based on a beam angle of at least one of the one or more light emitters.

In some examples, a radiometric power of the light emitted by the one or more light emitters may be based on the distance that the surface is away from the substrate, based on a size of the surface, based on a microorganism to be inactivated, or based on a beam angle of at least one of the one or more light emitters.

In some examples, a light emitting device may comprise an array of light emitting subcomponents. The light emitting subcomponents may be configured to inactivate microorganisms on a surface a distance away from the light emitting subcomponents by emitting a light. The light may comprise a proportion of a spectral energy of the light, measured in a 380 nanometers (nm) to 420 nm wavelength range, greater than 50%. The light may comprise a FWHM emission spectrum of less than 20 nm and centered at a wavelength of approximately 405 nm to concentrate the spectral energy of the light and minimize energy associated with wavelengths that bleed into an ultraviolet wavelength range. The light may comprise an irradiance at the surface sufficient to initiate inactivation of microorganisms on the surface. The light emitting device may comprise a controller disposed on the substrate and configured to adjust output of the array of light emitting subcomponents.

In some examples, the controller may be configured to adjust, based on a time that the light emitted by the array of light emitting subcomponents has been emitted, a radiometric power of the light emitted by the array of light emitting subcomponents.

In some examples, the controller of the light emitting device may be configured to adjust the proportion of the spectral energy, measured in a 380 nm to 420 nm wavelength range, between 0% and 100%.

In some examples, the controller may be configured to determine the distance between the array of light emitting subcomponents and the surface and determine a size of the surface. The controller may be configured to determine, based on the determined distance between the array of light emitting subcomponents and the surface, based on the size of the surface, based on a microorganism to be inactivated, or based on a beam angle of at least one light emitting subcomponent, a number of light emitting subcomponents to inactivate the microorganism. The controller may be configured to power the determined number of light emitting subcomponents for a period of time.

In some examples, the light emitting subcomponents may be arranged based on the distance between array of light emitting subcomponents and the surface, based on a size of the surface, based on a microorganism to be inactivated, or based on a beam angle of at least one of the light emitting subcomponents.

In some examples, a radiometric power of the light emitted by the light emitting subcomponents may be based on a distance between the array of light emitting subcomponents and the surface, based on a size of the surface, based on a microorganism to be inactivated, or based on a beam angle of at least one of the light emitting subcomponents.

Approximating language, as used herein throughout the specification and claims, may be applied to modify any quantitative representation that could permissibly vary without resulting in a change in the basic function to which it is related. Accordingly, a value modified by a term or terms, such as "about", "approximately" and "substantially", are not to be limited to the precise value specified. Values identified herein may be varied between +/−10% of the stated value(s) and still function as described. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

The above disclosure sets forth various examples. Modifications of which may be made as desired for different implementations. For example, steps and/or components may be subdivided, combined, rearranged, removed, and/or augmented; performed on a single device or a plurality of devices; performed in parallel, in series; or any combination thereof. Additional features may be added.

We claim:

1. A light emitting device comprising:
   a substrate; and
   one or more light emitters disposed on the substrate and configured to emit a light to inactivate microorganisms on a solid surface a distance away from the substrate wherein the substrate is a circuit board comprising an on-board controller;
   wherein to emit the light, the one or more light emitters are further configured to produce a radiometric power that satisfies a threshold, wherein the threshold is based on a target irradiance at the solid surface sufficient to initiate inactivation of the microorganisms on the solid surface, wherein the target irradiance is approximately 1 milliwatt per square centimeter (mW/cm$^2$) across at least a portion of the solid surface;
   wherein the radiometric power is based on:
      a number of the one or more light emitters,
      beam angles of the one or more light emitters, and
      the distance; and
   wherein the light emitted by the one or more light emitters comprises:
      a proportion of a spectral energy of the light, measured in a 380 nanometers (nm) to 420 nm wavelength range, of at least 50%; and
      a full width half max (FWHM) emission spectrum of less than 20 nm and centered at a wavelength of approximately 405 nm to concentrate the spectral energy of the light and minimize energy associated with wavelengths that bleed into an ultraviolet wavelength range.

2. The light emitting device of claim 1, wherein the number of the one or more light emitters is at least two, and wherein the one or more light emitters are arranged on the substrate to provide a substantially uniform irradiance across the solid surface.

3. The light emitting device of claim 1, further comprising:
   a sensor configured to detect occupancy of an area comprising the solid surface; and
   a second controller configured to adjust, based on the sensor detecting occupancy of the area, the proportion of the spectral energy, measured in the 380 nm to 420 nm wavelength range, of the light between 50% and 100%.

4. The light emitting device of claim 1, wherein the target irradiance comprises an exposure time of about 48 hours.

5. The light emitting device of claim 1, wherein the substrate comprises one or more of aluminum, glass-reinforced epoxy laminate, Teflon, polyimide, or copper.

6. The light emitting device of claim 1, wherein at least one of the one or more light emitters comprises a light emitting diode (LED).

7. The light emitting device of claim 1, wherein the number of the one or more light emitters is at least two, and wherein the one or more light emitters are configured in an array.

8. The light emitting device of claim 1, wherein the target irradiance is based on a size of the solid surface, a microorganism to be inactivated, or a minimum irradiance sufficient to initiate inactivation of the microorganisms on the solid surface.

9. The light emitting device of claim 1, wherein the number of the one or more light emitters is at least two, and wherein the one or more light emitters are arranged on the substrate based on the distance, a size of the solid surface, or the beam angles of the one or more light emitters.

10. The light emitting device of claim 1, wherein the number of the one or more light emitters is at least two, and wherein the one or more light emitters are arranged on the substrate to provide a minimum irradiance at the solid surface of at least 50% of a maximum irradiance at the solid surface.

11. The light emitting device of claim 1, wherein the number of the one or more light emitters is at least two, and wherein the one or more light emitters are arranged on the substrate such that boundaries of the light emitted from neighboring light emitters of the one or more light emitters intersect at the solid surface.

12. The light emitting device of claim 1, wherein the number of the one or more light emitters is one.

13. The light emitting device of claim 1, wherein at least a portion of the light is normal to a portion of the solid surface.

14. The light emitting device of claim 1, wherein the one or more light emitters are configured in an array, wherein the array comprises a first linear light emitting subcomponent, a second linear light emitting subcomponent, and a third linear light emitting subcomponent, wherein the first, second, and third linear light emitting subcomponents are positioned parallel to each other, and wherein the first, second, and third linear light emitting subcomponents each further comprise a plurality of light emitters each configured to produce the target irradiance.

15. The light emitting device of claim 1, wherein the one or more light emitters are configured in a circular array, and wherein each of the one or more light emitters are configured to produce the target irradiance.

16. The light emitting device of claim 1, wherein the one or more light emitters are configured in an array, wherein the array comprises a plurality of linear light emitting subcomponents, wherein the plurality of linear light emitting subcomponents are positioned parallel to each other, and wherein the plurality of linear light emitting subcomponents each further comprise a plurality of light emitters each configured to produce the target irradiance.

17. The light emitting device of claim 1, wherein the on-board contoller further comprises a driving circuitry component that controls the output of the light.

18. The light emitting device of claim 1, wherein the substrate is disposed behind a diffuser, and wherein the lens allows for at least 75% of the light within the range of 380-420 nm to transmit through.

19. The light emitting device of claim 1, wherein the circuit board is in the form of a circle with a hole in the middle.

20. The light emitting device of claim 19, wherein the circuit board is a printed circuit board.

21. The light emitting device of claim 1, wherein the substrate is a printed circuit board.

22. The light emitting device of claim 1, wherein the controller is configured to continuously emit the light at the radiometric power that satisfies the threshold.

23. The light emitting device of claim 1, wherein the one or more light emitters further comprise a conformal coating.

24. A light emitting device comprising:
a substrate wherein the substrate is a circuit board further comprising an on-board controller and wherein the circuit board is in the form of a circle with a hole in the middle; and
a plurality of light emitters disposed on the substrate and configured to emit a light to inactivate microorganisms on a surface a distance away from the substrate;
wherein to emit the light, the plurality of light emitters are further configured to produce a radiometric power that satisfies a threshold, wherein the threshold is based on a target irradiance at the solid surface sufficient to initiate inactivation of the microorganisms on the surface;
wherein the radiometric power is based on:
a number of the one or more light emitters,
beam angles of the one or more light emitters, and
the distance; and
wherein the light emitted by the plurality of light emitters comprises:
a proportion of a spectral energy of the light, measured in a 380 nanometers (nm) to 420 nm wavelength range, of at least 50%; and
a full width half max (FWHM) emission spectrum of less than 20 nm and centered at a wavelength of approximately 405 nm to concentrate the spectral energy of the light and minimize energy associated with wavelengths that bleed into an ultraviolet wavelength range.

* * * * *